(12) United States Patent
Ogasawara et al.

(10) Patent No.: US 12,023,140 B2
(45) Date of Patent: Jul. 2, 2024

(54) BIOLOGICAL INFORMATION ANALYSIS DEVICE, BIOLOGICAL INFORMATION ANALYSIS METHOD, AND BIOLOGICAL INFORMATION ANALYSIS SYSTEM

(71) Applicant: Nippon Telegraph and Telephone Corporation, Tokyo (JP)

(72) Inventors: Takayuki Ogasawara, Tokyo (JP); Rieko Sato, Tokyo (JP); Kenichi Matsunaga, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 656 days.

(21) Appl. No.: 17/276,193

(22) PCT Filed: Sep. 20, 2019

(86) PCT No.: PCT/JP2019/036974
§ 371 (c)(1),
(2) Date: Mar. 15, 2021

(87) PCT Pub. No.: WO2020/071156
PCT Pub. Date: Apr. 9, 2020

(65) Prior Publication Data
US 2021/0338089 A1    Nov. 4, 2021

(30) Foreign Application Priority Data
Oct. 4, 2018 (JP) ................. 2018-188909

(51) Int. Cl.
*A61B 5/0245* (2006.01)
*A61B 5/00* (2006.01)

(52) U.S. Cl.
CPC .......... *A61B 5/0245* (2013.01); *A61B 5/7246* (2013.01); *A61B 5/742* (2013.01); *A61B 2562/0219* (2013.01)

(58) Field of Classification Search
None
See application file for complete search history.

(56) References Cited

U.S. PATENT DOCUMENTS

| 2015/0119748 A1 | 4/2015 | Lai |
| 2018/0042486 A1 * | 2/2018 | Yoshizawa ......... A61B 5/02125 |
| 2019/0050747 A1 * | 2/2019 | Nakamura .......... G06F 11/0775 |

FOREIGN PATENT DOCUMENTS

| JP | 201585199 A | 5/2015 |
| WO | WO-2017154844 A1 * | 9/2017 .......... G06F 11/0775 |

OTHER PUBLICATIONS

Naoko Kasai, et al., "Development of hitoe, a functional material that makes it possible to measure biological," Development of Functional Tex River e "hitoe": Wearable Electrodes for Vionitoring Human Vital Signals, Institute of Electronics, Information and Communication Engineers, Summer 2017, 15 pages.

(Continued)

*Primary Examiner* — Ankit D Tejani
(74) *Attorney, Agent, or Firm* — Slater Matsil, LLP

(57) ABSTRACT

A biological information analysis apparatus includes a sensor data acquirer that acquires biological information of a user measured by a sensor, a data analyzer that analyzes time-series data for the biological information over a plurality of time intervals and, from multiple pieces of biological information that were acquired at mutually corresponding times of measurement in respective ones of the plurality of time intervals, calculates representative values for the multiple pieces of biological information, a measurement anomaly detector that detects an anomaly contained in the measured biological information based on time-series data with the representative values calculated by the data analyzer or on the time-series data for the multiple pieces of biological information that was used in calculation of the time-series data with the representative values, and a pre- (Continued)

senter that outputs the calculated representative values for the multiple pieces of biological information and information indicating the detected anomaly.

13 Claims, 10 Drawing Sheets

(56) References Cited

OTHER PUBLICATIONS

Tetsuro Sugihara, "Error and number n," http://heartland.geocities.jp/ecodata222/ed/edj 1-7-1-5.html, Aug. 22, 2018, 7 pages.

* cited by examiner

BIOLOGICAL INFORMATION ANALYSIS DEVICE, BIOLOGICAL INFORMATION ANALYSIS METHOD, AND BIOLOGICAL INFORMATION ANALYSIS SYSTEM

CROSS-REFERENCE TO RELATED APPLICATIONS

This patent application is a national phase filing under section 371 of PCT/JP2019/036974, filed Sep. 20, 2019, which claims the priority of Japanese patent application no. 2018-188909, filed Oct. 4, 2018, each of which is incorporated herein by reference in its entirety.

TECHNICAL FIELD

The present invention relates to a biological information analysis apparatus, a biological information analysis method, and a biological information analysis system, and in particular to techniques for analyzing biological information measured by a sensor worn by a user.

BACKGROUND

In recent years, biological information such as heart rate and acceleration measured by wearable devices and the like has been utilized in the fields of sports and medicine. For example, Non-Patent Literature 1 discloses a technique for stably measuring the heart rate and/or electrocardiographic waveforms of a user wearing a wearable biological electrode inner which is made of fiber conductive material over a long period of time. Non-Patent Literature 1 also discloses a technique for estimating the posture or gait of the user based on measurement data from an acceleration sensor contained in a wearable device worn by the user.

CITATION LIST

Non-Patent Literature

Non-Patent Literature 1: Kasai, Ogasawara, Nakashima, and Tsukada, "Development of Functional Textile "hitoe": Wearable Electrodes for Monitoring Human Vital Signals", The Institute of Electronics, Information and Communication Engineers, Communications Society Magazine No. 41 (June 2017) (Vol. 11 No. 1)

Non-Patent Literature 2: Sugihara Tetsuro, "Errors and Sample Number", [online], [searched on Sep. 20, 2018], the Internet <http://heartland.geocities.jp/ecodata222/ed/edj1-7-1-5.html>

SUMMARY

Technical Problem

Conventional techniques are capable of measuring the user's biological information continuously and stably. However, the daily activities of the user are not always the same every day. Thus, in some cases such as when daily variations are present, it is difficult to ascertain an occurrence of an anomaly contained in measured biological information.

Embodiments of the present invention have been made in order to solve such a problem and an object thereof is to provide a biological information analysis apparatus, a biological information analysis method, and a biological information analysis system that can ascertain an occurrence of an anomaly contained in measured biological information.

Means for Solving the Problem

In order to solve the problem, a biological information analysis apparatus according to embodiments of the present invention includes: a sensor data acquisition unit that acquires biological information measured by a sensor; a data analysis unit that analyzes time-series data for the biological information over a plurality of time intervals and, from multiple pieces of biological information that were acquired at mutually corresponding times of measurement in respective ones of the plurality of time intervals, calculates representative values for these multiple pieces of biological information; a measurement anomaly detection unit that detects an anomaly contained in the measured biological information based on time-series data with the representative values calculated by the data analysis unit or on the time-series data for the multiple pieces of biological information that was used in calculation of the time-series data with the representative values; and a presentation unit that outputs the calculated representative values for the multiple pieces of biological information and information indicating the detected anomaly.

The biological information analysis apparatus according to embodiments of the present invention may further include an outlier determination unit that determines whether the multiple pieces of biological information contain outliers or not based on a preset criterion, and the measurement anomaly detection unit may detect as the anomaly that a proportion of outliers contained in the time-series data for the multiple pieces of biological information exceeds a predetermined value.

The biological information analysis apparatus according to embodiments of the present invention may further include an outlier determination unit that determines whether the multiple pieces of biological information contain outliers or not based on a preset criterion. When the outlier determination unit determines that outliers are contained, the data analysis unit may calculate representative values for multiple pieces of biological information that were acquired at mutually corresponding times of measurement in respective ones of the plurality of time intervals, from these multiple pieces of biological information excluding the outliers, and the measurement anomaly detection unit may detect as the anomaly that an output period during which time-series data with the representative values was actually output by the data analysis unit is short relative to a predefined output period, regarding the output period during which the time-series data with the representative values is output.

In the biological information analysis apparatus according to embodiments of the present invention, the data analysis unit may calculate averages of the multiple pieces of biological information as the representative values, and the biological information analysis apparatus may further include a first summarization unit that calculates summary values which statistically summarize the multiple pieces of biological information for each given period included in the plurality of time intervals based on time-series data with the averages of the multiple pieces of biological information, and the measurement anomaly detection unit may detect as the anomaly that the averages are statistically insufficient for calculation of summary values when the first summarization unit is to calculate the summary values.

The biological information analysis apparatus according to embodiments of the present invention may further include a second summarization unit that calculates biological state information being a qualitative variable based on the time-series data for the biological information over the plurality of time intervals, and calculate summary values which statistically summarize the biological state information based on an occurrence ratio of values of the biological state information at mutually corresponding times of measurement in the respective ones of the plurality of time intervals, and the measurement anomaly detection unit may detect as the anomaly that the occurrence ratio of values of biological state information is statistically insufficient for calculation of summary values when the second summarization unit is to calculate the summary values.

In the biological information analysis apparatus according to embodiments of the present invention, the measurement anomaly detection unit may detect as the anomaly that behavior of the time-series data with the representative values calculated by the data analysis unit falls outside or fits in a predefined reference range.

In order to solve the problem, a biological information analysis method according to embodiments of the present invention includes: a sensor data acquisition step of acquiring biological information measured by a sensor; a data analysis step of analyzing time-series data for the biological information over a plurality of time intervals and, from multiple pieces of biological information that were acquired at mutually corresponding times of measurement in respective ones of the plurality of time intervals, calculating representative values for these multiple pieces of biological information; a measurement anomaly detection step of detecting an anomaly contained in the measured biological information based on time-series data with the representative values calculated at the data analysis step or on the time-series data for the multiple pieces of biological information that was used in calculation of the time-series data with the representative values; and a presentation step of outputting the calculated representative values for the multiple pieces of biological information and information indicating the detected anomaly.

In order to solve the problem, a biological information analysis system according to embodiments of the present invention includes: a sensor terminal that outputs biological information measured by a sensor worn by a user to outside; a relay terminal that receives the biological information output by the sensor terminal and outputs the received biological information to outside; and an external terminal that receives the biological information output by the sensor terminal or by the relay terminal and causes the received biological information to be displayed on a display device. At least one of the sensor terminal, the relay terminal, and the external terminal includes: a sensor data acquisition unit that acquires the biological information; a data analysis unit that analyzes time-series data for the biological information over a plurality of time intervals and, from multiple pieces of biological information that were acquired at mutually corresponding times of measurement in respective ones of the plurality of time intervals, calculates representative values for these multiple pieces of biological information; a measurement anomaly detection unit that detects an anomaly contained in the measured biological information based on time-series data with the representative values calculated by the data analysis unit or on the time-series data for the multiple pieces of biological information that was used in calculation of the time-series data with the representative values; and a presentation unit that outputs the calculated representative values for the multiple pieces of biological information and information indicating the detected anomaly.

Effect of Embodiments of the Invention

According to embodiments of the present invention, an anomaly contained in multiple pieces of biological information is detected and information indicating the anomaly is presented based on representative values for the multiple pieces of biological information that are calculated from the multiple pieces of biological information that were acquired at mutually corresponding times of measurement in the respective ones of multiple time intervals. Thus, an occurrence of an anomaly contained in measured biological information can be ascertained.

DETAILED DESCRIPTION OF ILLUSTRATIVE EMBODIMENTS

Preferred embodiments of the present invention are now described in detail with reference to FIGS. 1 through 19.

First Embodiment

Figure 1:
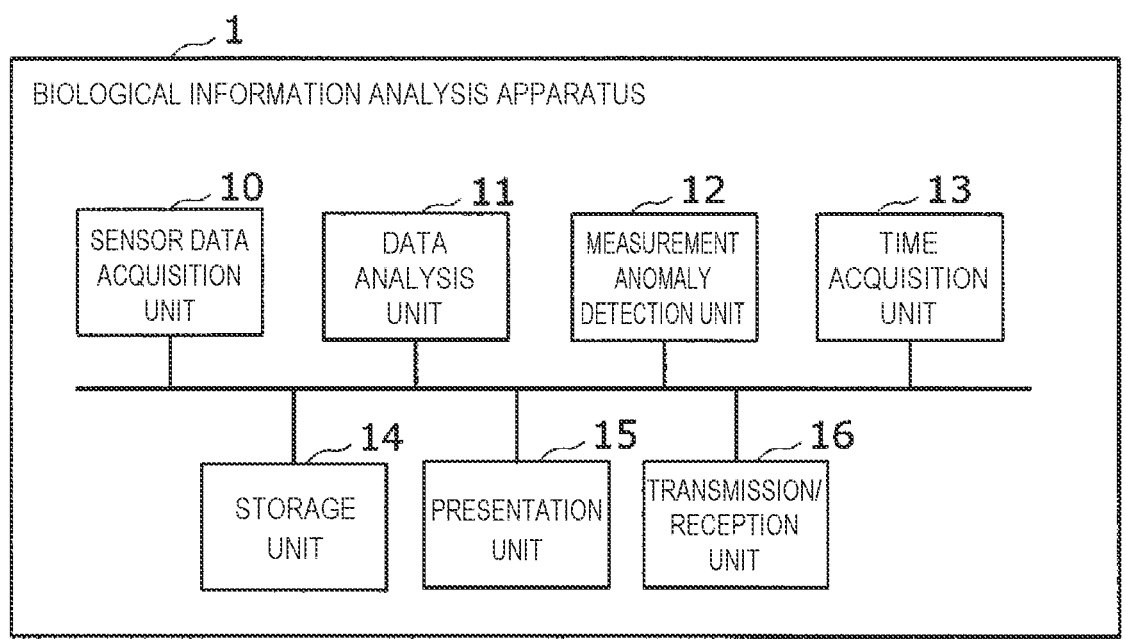
FIG. 1 is a block diagram showing a functional configuration of a biological information analysis apparatus according to a first embodiment of the present invention.

First, the configuration of a biological information analysis apparatus 1 according to a first embodiment of the present invention is generally described. FIG. 1 is a block diagram showing a functional configuration of the biological information analysis apparatus 1.

Functional Blocks of Biological Information Analysis Apparatus

The biological information analysis apparatus 1 includes a sensor data acquisition unit 10, a data analysis unit 11, a measurement anomaly detection unit 12, a time acquisition unit 13, a storage unit 14, a presentation unit 15, and a transmission/reception unit 16.

The sensor data acquisition unit 10 acquires biological information of a user measured by a sensor 105 worn by the user as discussed later. More specifically, when a heart rate meter is worn by the user as the sensor 105, for example, the sensor data acquisition unit 10 calculates a heart rate from electrocardiographic waveforms which are based on cardiac potentials measured by the heart rate meter. When an acceleration sensor is worn by the user as the sensor 105, the sensor data acquisition unit 10 converts an analog acceleration signal measured by the acceleration sensor to a digital signal at a predetermined sampling rate.

The sensor data acquisition unit 10 outputs time-series data in which the heart rate or the acceleration signal in the form of digital data and times of measurement are associated with each other. In this example, the heart rate and the acceleration data constitute biological information. The time-series data for the biological information measured by the sensor data acquisition unit 10 is stored in the storage unit 14, which is discussed later.

The data analysis unit 11 analyzes the time-series data for the biological information of the user acquired by the sensor data acquisition unit 10, and from multiple pieces of biological information that were acquired at mutually corresponding times of measurement in the respective ones of multiple time intervals, calculates representative values indicating typical values of these multiple pieces of biological information. For the time interval, a desired length of time can be set, such as one minute, one hour, one day, one month, and one year.

The data analysis unit 11 also calculates averages of the multiple pieces of biological information that were acquired at mutually corresponding times of measurement in the respective ones of multiple time intervals as representative values, based on the time-series data for biological information acquired by the sensor data acquisition unit 10. As an example, when the time interval is set to one day, the data analysis unit 11 calculates an average of multiple pieces of biological information that were measured at the same time of day on each day as a representative value from time-series data for biological information spanning multiple days.

As another example, when the time interval is set to one hour, the data analysis unit 11 may calculate an average of multiple pieces of biological information that were measured at the same time of day in units of minutes in each time interval from time-series data for biological information spanning multiple hours. As yet another example, when the time interval is set to one minute, the data analysis unit 11 may calculate an average of multiple pieces of biological information that were measured at the same time of day in units of seconds in each time interval from time-series data for biological information spanning multiple minutes.

Multiple pieces of biological information that were measured at mutually corresponding times of measurement from which the data analysis unit 11 calculates representative values of biological information need not be pieces of biological information that were sampled at strictly the same time, but may be pieces of biological information that were measured within a temporal range that can be considered to be proximate.

The measurement anomaly detection unit 12 detects an anomaly contained in the measured biological information based on the time-series data with the representative values calculated by the data analysis unit 11 or on the time-series data for the multiple pieces of biological information that was used for the calculation of the time-series data with representative values. For example, when the time interval is set to one day, the measurement anomaly detection unit 12 detects outliers contained in the time-series data with the averages of the multiple pieces of biological information that were measured at the same time of day on each day as calculated by the data analysis unit 11, from time-series data for biological information spanning multiple days.

An anomaly to be detected by the measurement anomaly detection unit 12 refers to a situation where conditions required for obtaining meaningful representative values are not satisfied when the data analysis unit 11 is to calculate representative values for multiple pieces of biological information.

The time acquisition unit 13 acquires a reference time to be used in the biological information analysis apparatus 1. The time acquisition unit 13 may acquire time information from a clock 107 included in the biological information analysis apparatus 1 or instead from a time server not illustrated, for example. The time information acquired by the time acquisition unit 13 is used in the sampling of biological information by the sensor data acquisition unit 10 or in the calculation of representative values of biological information by the data analysis unit 11.

The storage unit 14 stores time-series data for biological information of the user acquired by the sensor data acquisition unit 10. The storage unit 14 also stores setting information related to the time interval and the representative values of biological information calculated by the data analysis unit 11.

The presentation unit 15 outputs the representative values for multiple pieces of biological information calculated by the data analysis unit 11 and information indicating the anomaly detected by the measurement anomaly detection unit 12. More particularly, the presentation unit 15 causes the representative values and/or the information indicating the detected anomaly to be displayed on a display device 109, which is discussed later. The presentation unit 15 may present the information indicating the anomaly in a manner perceivable by the user, such as via an image, sound, and tactile sense.

The presentation unit 15 may also generate and present information for assisting the user based on the representative values and/or the information indicating the anomaly. Then, the presentation unit 15 may output the information for assisting the user to the display device 109 or to an operation device (not shown), which is embodied by a sound output device, a light source, an actuator, a thermal instrument and the like.

The transmission/reception unit 16 receives sensor data indicating the biological information measured by the sensor 105, which is discussed below. The transmission/reception unit 16 can also send the representative values for multiple pieces of biological information calculated by the data analysis unit 11 and/or information indicating the anomaly detected by the measurement anomaly detection unit 12 to the outside over a communication network.

Hardware Configuration of Biological Information Analysis Apparatus

Figure 2:
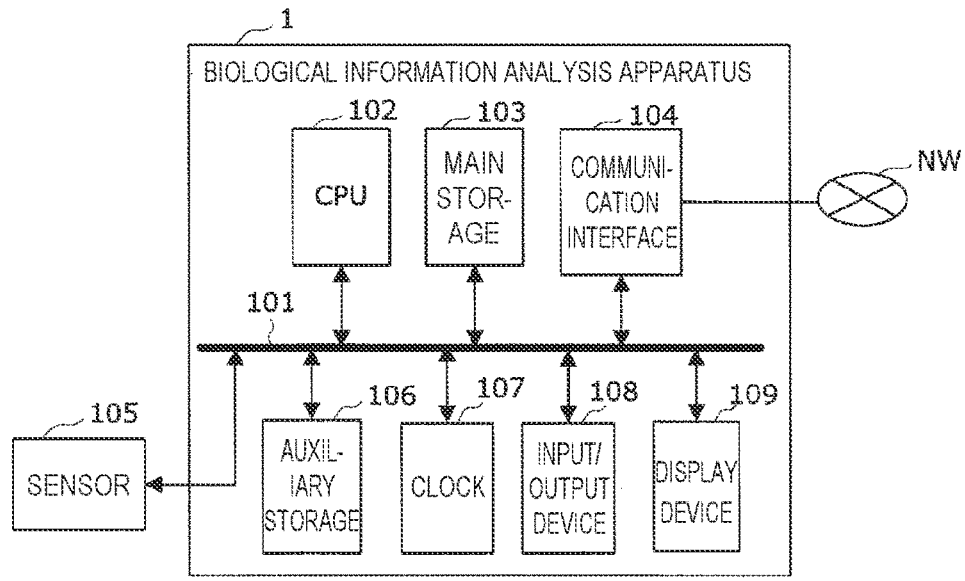
FIG. 2 is a block diagram showing a hardware configuration of the biological information analysis apparatus according to the first embodiment.

Next, an exemplary hardware configuration of the biological information analysis apparatus 1 having the aforementioned functions is described with the block diagram of FIG. 2.

As shown in FIG. 2, the biological information analysis apparatus 1 can be implemented by a computer including a CPU 102, a main storage 103, a communication interface 104, an auxiliary storage 106, a clock 107, and an input/output device 108, which are interconnected via a bus 101, and a program for controlling these hardware resources, for example. The biological information analysis apparatus 1 has the externally provided sensor 105 connected with the display device 109 provided inside the biological information analysis apparatus 1 over the bus 101.

The main storage 103 pre-stores a program for the CPU 102 to perform various kinds of control and operations. The functions of the biological information analysis apparatus 1, including the data analysis unit 11 and the measurement anomaly detection unit 12 shown in FIG. 1, are implemented by the CPU 102 and the main storage 103.

The communication interface 104 is an interface circuit for performing communication with various external electronic appliances over a communication network NW.

For the communication interface 104, an arithmetic interface and an antenna which support wireless data communication standards such as LTE, 3G, wireless LAN, and Bluetooth (a registered trademark) are used, for example. The transmission/reception unit 16 described in FIG. 1 is embodied by the communication interface 104.

The sensor 105 is embodied by a sensor, such as a heart rate meter, an electrocardiograph and an acceleration sensor, for example. The sensor 105 is worn by the user for a preset measurement period and measures biological information such as the heart rate, acceleration and the like of the user.

The auxiliary storage 106 is composed of a readable-writable storage medium and a drive for writing and reading various kinds of information such as programs and data to/from the storage medium. For the auxiliary storage 106, a hard disk or semiconductor memory such as flash memory can be used as storage media.

The auxiliary storage 106 has a storage area for storing time-series data for biological information measured by the sensor 105 and a program storage area for storing a program for the biological information analysis apparatus 1 to perform analysis processing on the biological information. The storage unit 14 described in FIG. 1 is embodied by the auxiliary storage 106. The auxiliary storage 106 may further have a backup area for backing up such data and programs, for example.

The clock 107 is composed of an internal clock built in the computer and the like and measures time. Time information acquired by the clock 107 is used in the sampling of biological information and calculation of representative values. Time information obtained by the clock 107 will be acquired by the time acquisition unit 13 described in FIG. 1.

The input/output device 108 is composed of an I/O terminal which receives input of signals from external appliances such as the sensor 105 and the display device 109, and outputs signals to external appliances.

The display device 109 functions as the presentation unit 15 of the biological information analysis apparatus 1. The display device 109 is embodied by a liquid crystal display and the like. The display device 109 also constitutes an operation device for outputting user assistance information, which is generated based on representative values for biological information and/or information indicating an anomaly.

Biological Information Analysis Method

Figure 3:
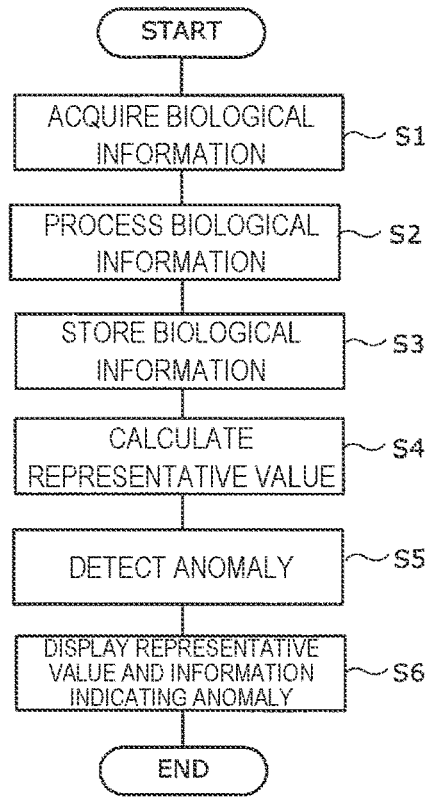
FIG. 3 is a flowchart illustrating a biological information analysis method according to the first embodiment.

Next, operation of the biological information analysis apparatus 1 having the above-described configuration is described with the flowchart of FIG. 3. First, the following processing is performed with the sensor 105 worn by the user. The following is described for a case where the user's heart rate is measured as biological information as a specific example.

The sensor data acquisition unit 10 acquires biological information measured by the sensor 105 worn by the user via the transmission/reception unit 16 (step S1). More specifically, when "one day" is set as the time interval, for example, the sensor data acquisition unit 10 acquires electrocardiographic waveforms of the user that were measured over multiple time intervals, e.g., two days. The acquired electrocardiographic waveforms for the two days are accumulated in the storage unit 14.

Next, the sensor data acquisition unit 10 performs removal of noise in the acquired biological information and also performs processing to convert the biological information as an analog signal to a digital signal (step S2). Specifically, the sensor data acquisition unit 10 performs removal of noise on the cardiac potentials measured by the sensor 105 composed of a heart rate meter by way of filtering, and also calculates a heart rate from electrocardiographic waveforms which are based on the cardiac potentials. Time-series data for the biological information processed by the sensor data acquisition unit 10 is stored in the storage unit 14 (step S3).

Next, the data analysis unit 11 calculates a representative value for multiple pieces of biological information (step S4). More specifically, for the time-series data of the user's heart rate over two days (two intervals), the data analysis unit 11 calculates an average of the heart rates that were acquired at mutually corresponding times of measurement on the first day and the second day as a representative value.

The data analysis unit 11 determines an average $A_t$ of time-series data for multiple pieces of biological information such as heart rates using Formula (1) below:

Formula 1

$$A_t = \frac{\sum_{i=1}^{N} X_{t,i}}{N} \quad (1)$$

In Formula (1), t is the time of measurement, where measurement is performed at a measurement frequency based on the sampling rate. N represents the number of days for which measurement was performed, namely the number of time intervals. This N will also indicate the number of data at mutually corresponding times of measurement on the respective ones of multiple time intervals. For example, N is N=2 when biological information is measured over two days. The term i is measurement date (time interval), corresponding to each measurement date. For example, given that the heart rate on the first day transitioned to 100 bpm and that on the second day transitioned to 60 bpm, the average $A_t$ will always be 80 bpm ((100+60)/2=80). Accordingly, the average of the heart rates at the mutually corresponding times of measurement on the two days will be 80 bpm.

By thus calculating an average of multiple pieces of biological information that were acquired at mutually corresponding times of measurement on the respective ones of multiple days, daily dispersions in the user's heart rate measured over multiple days (multiple time intervals) are mitigated, enabling acquisition of biological information measurements that are truly close to the user's habits or behavior.

Referring back to the flowchart of FIG. 3, the representative values for the user's biological information provided by the data analysis unit 11 are stored in the storage unit 14. Next, the measurement anomaly detection unit 12 detects an anomaly contained in the multiple pieces of biological information based on the representative value for the multiple pieces of biological information calculated by the data analysis unit 11 (step S5). Then, the presentation unit 15 causes the display device 109 to display the representative value for biological information calculated at step S4 and information indicating the anomaly detected at step S5 (step S6). The presentation unit 15 may also generate assistance information for the user based on the representative value and/or the information indicating the anomaly and cause it to be displayed on the display device 109 and the like.

The functions of the biological information analysis apparatus 1 described above may also be distributed among multiple computers that are communicatively interconnected via a communication network, aside from being provided in a single computer.

Biological Information Analysis System

Next, a biological information analysis system as a specific arrangement of the biological information analysis apparatus 1 according to the present invention will be described with reference to FIGS. 4 and 5.

Figure 4:
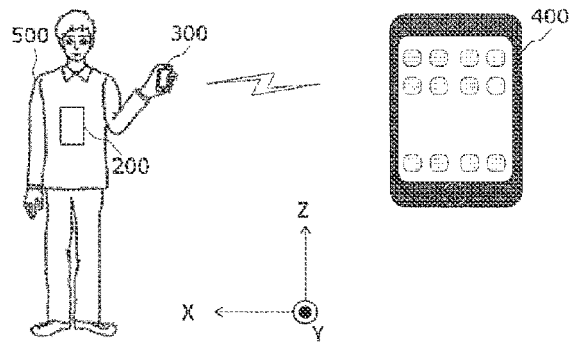
FIG. 4 is a diagram for generally describing a configuration of a biological information analysis system according to the first embodiment.

The biological information analysis system includes, for example, a sensor terminal 200 to be worn by a user 500, a relay terminal 300, and an external terminal 400, as shown in FIG. 4. All or some of the sensor terminal 200, the relay terminal 300 and the external terminal 400 have the functions of the biological information analysis apparatus 1, such as the data analysis unit 11 and measurement anomaly detection unit 12 described in FIG. 1. In the following, it is assumed that the relay terminal 300 includes the data analysis unit 11 and the measurement anomaly detection unit 12 described in FIG. 1 and the external terminal 400 includes the presentation unit 15 described in FIG. 1.

Functional Blocks of Sensor Terminal

The sensor terminal 200 includes a sensor 201, a sensor data acquisition unit 202, a data storage unit 203, and a data transmission unit 204. The sensor terminal 200 is placed on a trunk of the user 500's body, for example, to measure biological information over multiple time intervals. The sensor terminal 200 transmits the measured biological information of the user 500 to the relay terminal 300 over the communication network NW.

The sensor 201 is embodied by a heart rate meter, an acceleration sensor and the like. Three axes of the acceleration sensor included in the sensor 201 are set such that the X-axis is parallel to the right-left direction of the body, the Y-axis is to the front-back direction of the body, and the Z-axis is to the up-down direction of the body as shown in FIG. 4, for example. The sensor 201 corresponds to the sensor 105 described in FIG. 2.

The sensor data acquisition unit 202 acquires the biological information measured by the sensor 201. More particularly, the sensor data acquisition unit 202 performs removal of noise in the acquired biological information and sampling processing, and determines time-series data for the biological information in the form of a digital signal. The sensor data acquisition unit 202 corresponds to the sensor data acquisition unit 10 described in FIG. 1.

The data storage unit 203 stores time-series data for the biological information measured by the sensor 201 and time-series data for the biological information in the form of a digital signal resulting from processing by the sensor data acquisition unit 202. The data storage unit 203 corresponds to the storage unit 14 (FIG. 1).

The data transmission unit 204 transmits the time-series data for biological information stored in the data storage unit 203 to the relay terminal 300 over the communication network NW. The data transmission unit 204 includes a communication circuit for performing wireless communication which supports wireless data communication standards such as LTE, 3G, wireless LAN (Local Area Network), and Bluetooth (a registered trademark), for example. The data transmission unit 204 corresponds to the transmission/reception unit 16 (FIG. 1).

Functional Blocks of Relay Terminal

The relay terminal 300 includes a data reception unit 301, a data storage unit 302, a time acquisition unit 303, a data analysis unit 304, a measurement anomaly detection unit 305, and a data transmission unit 306. The relay terminal 300 analyzes the time-series data for the biological information of the user 500 measured over multiple time intervals received from the sensor terminal 200. The relay terminal 300 further calculates representative values for multiple pieces of biological information that were acquired at mutually corresponding times of measurement in respective ones of the multiple time intervals, from these multiple pieces of biological information. The relay terminal 300 also detects an anomaly contained in the measured biological information based on the calculated representative values for the biological information. The calculated representative values and the anomaly are transmitted to the external terminal 400.

The relay terminal 300 is embodied by a smartphone, a tablet, a notebook PC and the like.

The data reception unit 301 receives the time-series data for the biological information from the sensor terminal 200 over the communication network NW. The data reception unit 301 corresponds to the transmission/reception unit 16 (FIG. 1).

The data storage unit 302 stores the biological information of the user 500 received by the data reception unit 301 and the representative values for the biological information calculated by the data analysis unit 304. The data storage unit 302 also stores information on the anomaly detected by the measurement anomaly detection unit 305. The data storage unit 302 corresponds to the storage unit 14 (FIG. 1).

The time acquisition unit 303 retrieves time information to be used in analysis processing for the biological information by the data analysis unit 304 from the internal clock (the clock 107). The time acquisition unit 303 corresponds to the time acquisition unit 13 described in FIG. 1.

The data analysis unit 304 analyzes the time-series data for the biological information of the user 500 over multiple time intervals received by the data reception unit 301, and from multiple pieces of biological information that were acquired at mutually corresponding times of measurement in the respective ones of multiple time intervals, determines a representative value indicating a typical value of these multiple pieces of biological information. For example, an average of heart rates of the user 500 that were measured over multiple days in the same time slot is calculated using the Formula (1) described above. The calculated average of biological information is stored in the data storage unit 302. The data analysis unit 304 corresponds to the data analysis unit 11 described in FIG. 1.

The measurement anomaly detection unit 305 detects an anomaly contained in the measured biological information based on time-series data with the representative values calculated by the data analysis unit 304 or on time-series data for the multiple pieces of biological information that was used in the calculation of the representative values. The measurement anomaly detection unit 305 corresponds to the measurement anomaly detection unit 12 described in FIG. 1.

The data transmission unit 306 transmits the representative values of biological information calculated by the data analysis unit 304 and information indicating the anomaly detected by the measurement anomaly detection unit 305 to the external terminal 400 over the communication network NW. The data transmission unit 306 corresponds to the transmission/reception unit 16 (FIG. 1).

Functional Blocks of External Terminal

The external terminal 400 includes a data reception unit 401, a data storage unit 402, a presentation processing unit 403, and a presentation unit 404. The external terminal 400 presents the representative values for biological information of the user 500 and the information indicating the anomaly received from the relay terminal 300 over the communication network NW. The external terminal 400 also presents assistance information for the user 500 which is based on the representative values and/or the information indicating the anomaly.

The external terminal 400 is embodied by a smartphone, a tablet, a notebook PC and the like as with the relay terminal 300. The external terminal 400 has a display device for displaying the representative values and/or the information indicating the anomaly received.

The external terminal 400 also has an operation device (not shown) for outputting information to assist the user 500 which is generated based on the representative values and/or the information indicating the anomaly. Examples of the operation device provided in the external terminal 400 include a display device, a sound output device, a light source, an actuator, and a thermal instrument.

The sound output device can be a speaker or a musical instrument, for example. The light source can be an LED or a light bulb. The actuator can be a vibrator, a robot arm, or an electric therapy machine. The thermal instrument can be a heater, a Peltier device and the like.

The data reception unit 401 receives the representative values for biological information and/or the information indicating the anomaly from the relay terminal 300 over the communication network NW. The data reception unit 401 corresponds to the transmission/reception unit 16 (FIG. 1).

The data storage unit 402 stores the representative values for biological information and/or the information indicating the anomaly received by the data reception unit 401. The data storage unit 402 corresponds to the storage unit 14 (FIG. 1).

The presentation processing unit 403 controls a display format of the representative values for biological information and/or the information indicating the anomaly by means of a style sheet and the like. The presentation processing unit 403 also generates assistance information for the user 500 based on the representative values and/or the information indicating the anomaly. The presentation processing unit 403 corresponds to the presentation unit 15 described in FIG. 1.

The presentation unit 404 outputs the representative values for biological information and/or the information indicating the anomaly according to an instruction from the presentation processing unit 403. The presentation unit 404 also presents assistance information for the user 500 generated based on the representative values for biological information and/or the information indicating the anomaly. More particularly, the representative values and/or the information indicating the anomaly are displayed on the display device of the external terminal 400 in the form of textual information, a graph and the like.

The presentation unit 404 may also display the assistance information on the display device or output it via alert sound or the like from a speaker, not shown, provided in the external terminal 400. In addition, the presentation unit 404 can present the representative values and/or the information indicating the anomaly and the assistance information in a manner perceivable by the user 500, such as via vibration and light. The presentation unit 404 corresponds to the presentation unit 15 described in FIG. 1.

As described above, the biological information analysis system according to embodiments of the present invention is configured such that the functions of the biological information analysis apparatus 1 are distributed across the sensor terminal 200, the relay terminal 300 and the external terminal 400, and performs processing related to acquisition of biological information of the user 500, calculation of representative values, detection of an anomaly, and presentation of the representative values and information indicating the anomaly in a distributed manner.

Operational Sequence of Biological Information Analysis System

Next, the operation of the biological information analysis system having the above-described configuration will be described with the sequence diagram of FIG. 6.

Figure 6:
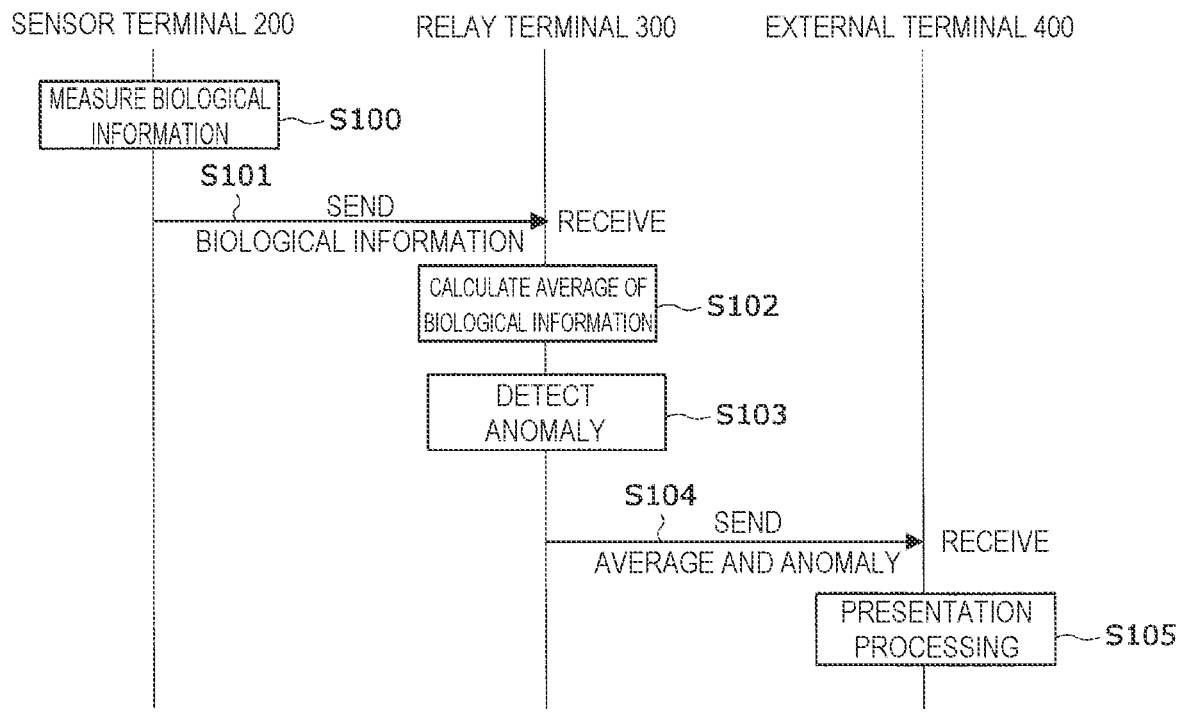
FIG. 6 is a sequence diagram for describing operations of the biological information analysis system according to the first embodiment.

As shown in FIG. 6, initially, the sensor terminal 200 is attached to the user 500 and measures biological information for multiple time intervals (step S100). The sensor terminal 200 determines a digital signal for the measured biological information and performs removal of noise, if necessary.

Next, the sensor terminal 200 transmits the biological information to the relay terminal 300 over the communication network NW (step S101). After receiving the time-series data for the biological information from the sensor terminal 200, the relay terminal 300 calculates an average as a representative value of the time-series data for the biological information (step S102). More particularly, the data analysis unit 304 of the relay terminal 300 uses Formula (1) to calculate an average of multiple pieces of biological information that were acquired at mutually corresponding times of measurement in respective ones of the multiple time intervals, from these multiple pieces of biological information.

Next, the measurement anomaly detection unit 305 detects an anomaly contained in the measured biological information based on the representative value calculated at step S102 (step S103). Then, the relay terminal 300 transmits the representative value for biological information and information indicating the detected anomaly to the external terminal 400 over the communication network NW (step S104). After receiving the representative value and the information indicating the anomaly, the external terminal 400 performs presentation processing (step S105). That is, the external terminal 400 controls a visual representation of the representative value and the information indicating the anomaly and causes it to be displayed on the display device 109. The external terminal 400 also generates assistance information for the user 500 based on the representative value and/or the information indicating the anomaly and causes it to be displayed on the display device 109 and the like.

As described above, the biological information analysis apparatus 1 according to the first embodiment performs analysis on multiple pieces of biological information such as the heart rates of the user 500 that were measured over multiple time intervals, and calculates representative values for multiple pieces of biological information that were acquired at mutually corresponding times of measurement. The biological information analysis apparatus 1 also detects an anomaly contained in biological information based on the time-series data with the calculated representative values for the multiple pieces of biological information. Thus, it is possible to detect an anomaly contained in the measured biological information of the user even when there are variations in the value of biological information from one time interval, such as a "day", to another.

Second Embodiment

A second embodiment of the present invention is now described. In the following descriptions, the same components as those in the first embodiment are denoted with the same reference numerals and description thereof is omitted.

The first embodiment showed a case where the measurement anomaly detection unit 12 detects an anomaly contained in measured biological information based on the time-series data with the representative values calculated by the data analysis unit 11. In contrast, a biological information analysis apparatus 1A according to the second embodiment further includes a summarization unit 17 (a first summarization unit and a second summarization unit) that statistically summarizes biological information. Then, the measurement anomaly detection unit 12 detects as an anomaly that the representative values such as the averages of biological information are statistically insufficient for calculation of summary values when the summarization unit 17 is to determine the summary values. The second embodiment is described below focusing on different arrangements from the first embodiment.

Figure 7:
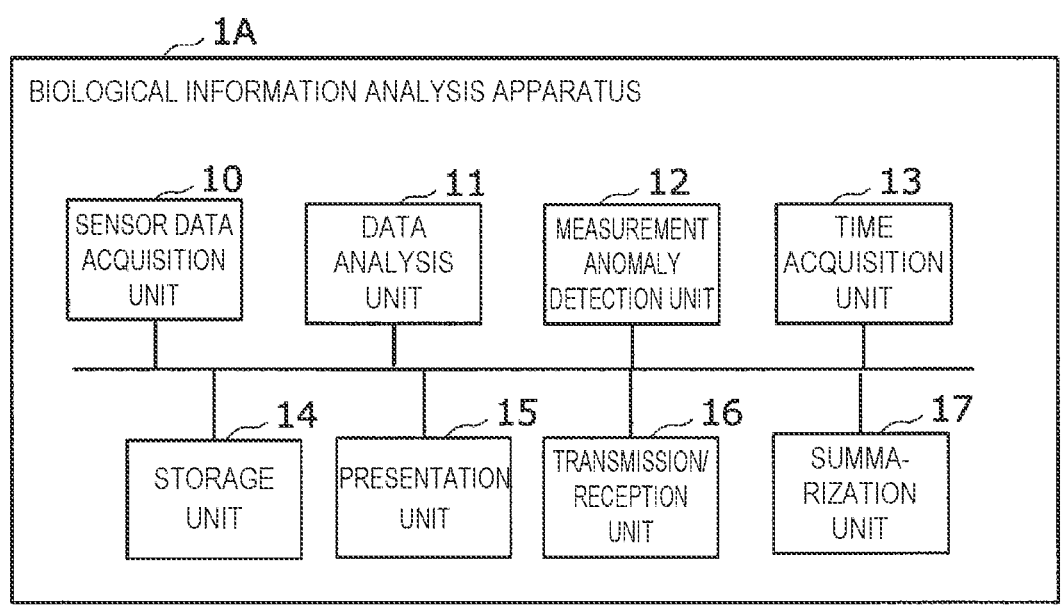
FIG. 7 is a block diagram showing a functional configuration of a biological information analysis apparatus according to a second embodiment.

As shown in FIG. 7, the biological information analysis apparatus 1A further includes the summarization unit 17.

The summarization unit 17 calculates statistical summary values based on the averages of biological information calculated by the data analysis unit 11. More particularly, the summarization unit 17 (the first summarization unit) calculates summary values which statistically summarize biological information over a given period on the basis of the time-series data with the averages of the biological information calculated by the data analysis unit 11. The summary values calculated by the summarization unit 17 include at least one of a cumulative value, an average, a breakdown showing proportions occupied by the values of given biological information in time intervals over which biological information is measured, a median, 25%-level, 75%-level, a standard deviation, and a standard error.

The summarization unit 17 (the second summarization unit) also calculates summary values which statistically summarize biological state information indicating a qualitative variable (hereinafter, sometimes called "biological state information") based on the occurrence ratio of the values thereof. More particularly, the summarization unit 17 calculates biological state information as a qualitative variable from the time-series data for the biological information acquired by the sensor data acquisition unit 10, and calculates summary values which statistically summarize the biological state information based on the occurrence ratio of the values of the biological state information at mutually corresponding times of measurement in the respective ones of multiple time intervals.

Here, biological state information is a qualitative variable. Biological state information is information showing the posture or state of the user, for example, and is a variable that cannot assume an intermediate value in averages of time-series data. In contrast, biological information like heart rate is a so-called quantitative variable, thus allowing calculation of an average represented by an intermediate value in time-series data. For example, when a state of the user being couched (lying down) is represented as "0" and being in an upright state, such as in a standing position, is represented as "1", biological state information has a property of being classified into either one of the two values. However, for the biological state information handled in this embodiment, an intermediate value like "0.5" in the example of the user's posture is not meaningful.

The summarization unit 17 sets the average to the same value if pieces of biological state information that were acquired at mutually corresponding times of measurement on multiple time intervals (multiple days) have the same value. In contrast, if pieces of biological state information at mutually corresponding times of measurement on multiple days are of different values, it divides the measurement period according to the proportions of the respective values.

For example, in biological state information measured on the first day (the first interval), if the user was in an upright state from 0 to 12 o'clock, the biological state information is set to "1" and, from 12 to 24 o'clock, it is set to "0" indicating a couched state. Likewise, for biological state information on the second day (the second interval), if the user was in an upright state in the time slots from 0 to 6 o'clock and from 12 to 18 o'clock, the biological state information is set to "1", and if the user was in a couched state in the time slots from 6 to 12 o'clock and from 18 to 24 o'clock, it is set to "0", for example.

The summarization unit 17 also calculates a state indicating an average of the biological state information for the two days (two intervals). For example, the states indicated by the biological state information from 0 to 6 o'clock and from 18 to 24 o'clock within one day (one interval) have the same values on the first and second days, so the same values will be calculated for both the first and the second days, respectively.

By contrast, in the above example, the values for the first and the second days are different from each other in the time slots from 6 to 12 o'clock and from 12 to 18 o'clock. Thus, each of the periods from 6 to 12 o'clock and from 12 to 18 o'clock is divided into two and "1" is assigned as the state in the time slot from 6 to 9 o'clock and "0" is assigned as the state in the time slot from 9 to 12 o'clock.

Similarly, the time slot from 12 to 18 o'clock is also divided into two and the states "1" and "0" are assigned in combination.

The summarization unit 17 determines an average of values indicating biological state information by way of division of time as described above. The summarization unit 17 also calculates summary values which statistically summarize biological state information based on the occurrence ratio of values showing the average of biological state information determined by division of time.

More specifically, the summarization unit 17 calculates a summary to the effect that "the states of 1 and 0 were each assumed for 50% of time within one day (one interval)". Note that the values indicating states are not limited to two values but similar calculation is also possible with three or more values. For example, if the states assume the three values "0, 1, 2" and a combination of "0, 0, 1" exists for 30 minutes, the occurrence ratio of "0" and "1" is "2:1", so that a summary would be calculated such that "0 was assumed for 20 minutes and 1 was assumed for 10 minutes". That is, given that k states are $P_1, P_2, \ldots P_k$, where j and k are integers and N is a real number, and if such a combination takes place for the amount of time of N, the occurrence ratio per state will be N/k. However, if there are j states that can be regarded as the same among k states, the occurrence ratio will be jN/k because they can be summed up.

The measurement anomaly detection unit 12 detects as an anomaly that representative values calculated by the data analysis unit 11 are statistically insufficient for calculation of summary values when the summarization unit 17 is to determine summary values. For example, if the size of statistical samples in time-series data with the averages of biological information such as the heart rate calculated by the data analysis unit 11 does not satisfy a sample size that can ensure statistically sufficient accuracy, the measurement anomaly detection unit 12 detects it as an anomaly.

Also, when the summary values calculated by the summarization unit 17 are summary values for biological state information that is associated with a qualitative variable like the user's state, the measurement anomaly detection unit 12 similarly detects as an anomaly that the occurrence ratio of values of biological state information is statistically insufficient for calculation of summary values.

The presentation unit 15 outputs information indicating the anomaly detected by the measurement anomaly detection unit 12 along with the summary values calculated by the summarization unit 17.

Figure 9:
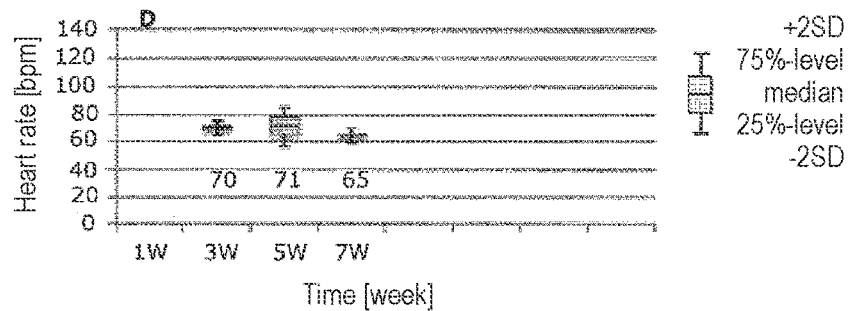
FIG. 9 is a diagram for describing an exemplary presentation of summary values according to the second embodiment.

FIG. 9 shows an example of summary values for biological information displayed by the presentation unit 15 on the display device 109. As shown in FIG. 9, the presentation unit 15 may display summary values for the heart rate as box plots of the heart rate from the first through the seventh weeks of the measurement period on the display device 109. The horizontal axis in FIG. 9 indicates time (week) and the vertical axis indicates the heart rate (bpm). In the figure, the 75%-level, average, and 25%-level of the heart rate are shown by boxes and a range of twice the positive and negative standard deviation (±2SD) is shown by whiskers.

For calculating statistical summary values represented by the standard deviation as shown in FIG. 9, a size of a certain number of samples is necessary. For example, Non-Patent Literature 2 makes assertions such as "n needs to be 10 or greater", "n of 30 is still insecure", and "n should be 100 at least", in relation to the sample size (n number) in determining the standard deviation.

In order to ensure such reliability regarding the sample size, a certain number, e.g., a threshold, may be set to 10 for the number of calculated averages or data, and if the number does not satisfy 10, a label "D", for example, may be presented as information indicating an anomaly with the corresponding summary values as shown in FIG. 9. The number of 10 as a certain number of data is illustrative; any sample size that can ensure statistically sufficient accuracy may be adopted.

By thus detecting and presenting the fact that a statistically sufficient sample size has not been obtained as an anomaly, the user and the like can be prompted to recognize that the sample size is not sufficient. It also serves to indicate the possibility of inadequate handling of the sensor 105 and the like in measurement of biological information. In such a case, the user could be prompted to remedy the inadequate handling of the sensor 105.

Operational Sequence of Biological Information Analysis System

Figure 5:
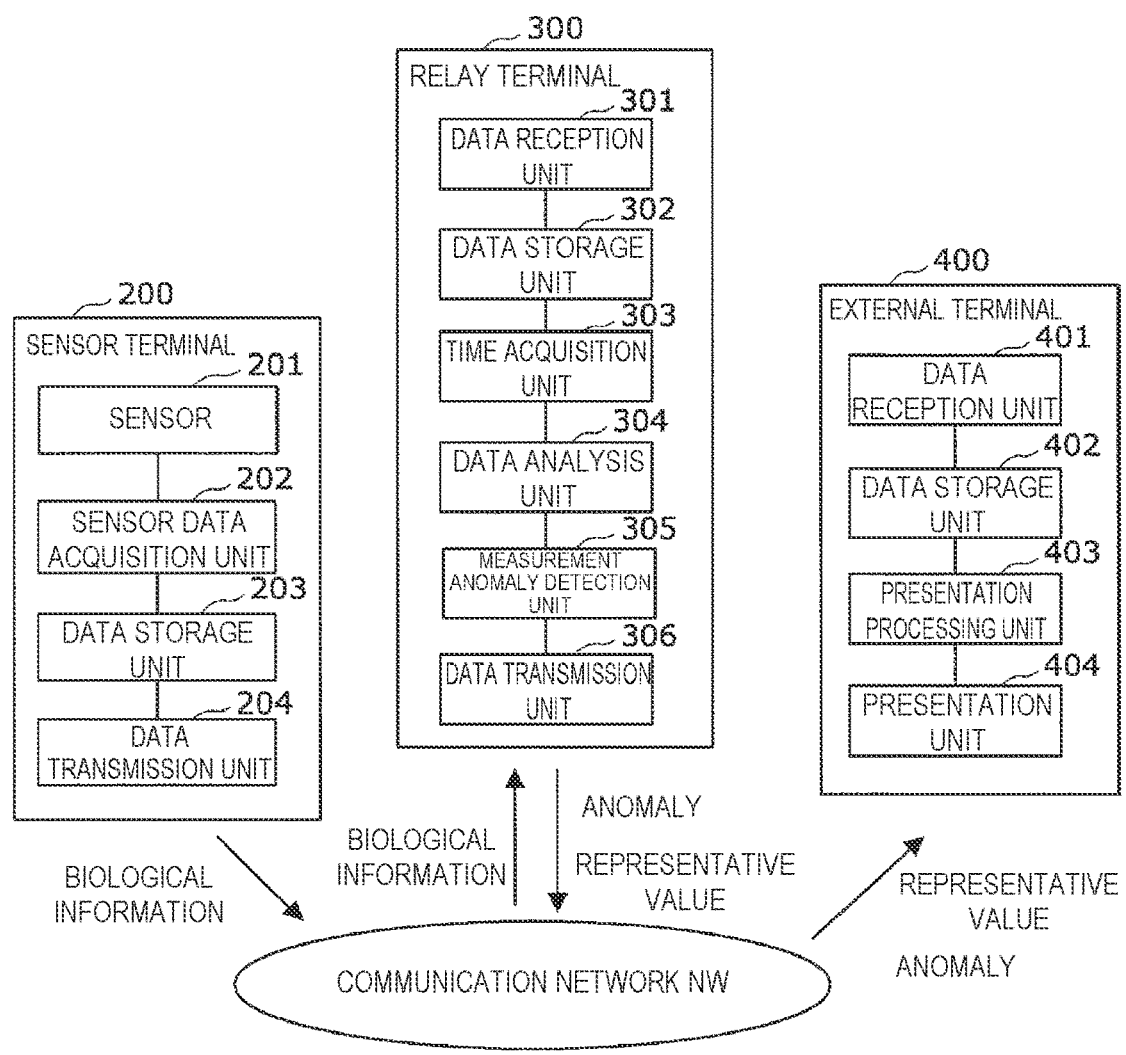
FIG. 5 is a block diagram showing the configuration of the biological information analysis system according to the first embodiment.
Figure 8:
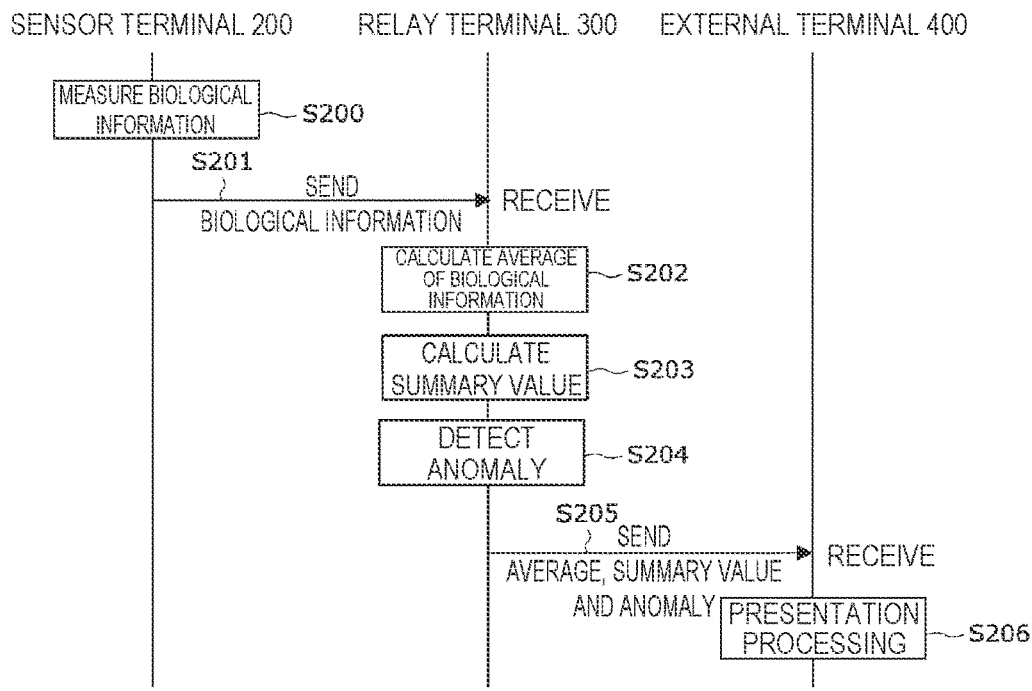
FIG. 8 is a sequence diagram illustrating operations of the biological information analysis system according to the second embodiment.

Next, operations in a case where the functions of the biological information analysis apparatus 1A according to this embodiment are implemented by a biological information analysis system including the sensor terminal 200, the relay terminal 300 and the external terminal 400 described in FIG. 5 are described with reference to the sequence diagram shown in FIG. 8. The respective functional blocks of the sensor terminal 200, the relay terminal 300, and the external terminal 400 are similar to the configurations described in FIG. 5. It is assumed that the relay terminal 300 includes the data analysis unit 11, the measurement anomaly detection unit 12 and the summarization unit 17, and the external terminal 400 includes the presentation unit 15.

Initially, the sensor terminal 200 is attached to the user 500 and measures biological information of the user 500 for multiple time intervals (step S200). More specifically, the sensor terminal 200 measures the cardiac potentials of the user 500 with a heart rate meter (the sensor 201), for example. The sensor data acquisition unit 202 acquires the cardiac potentials from the sensor 201 and calculates a heart rate from electrocardiographic waveforms which are based on the cardiac potentials. The acquired cardiac potentials and the heart rate are stored in the data storage unit 203.

Next, the sensor terminal 200 transmits the measured biological information to the relay terminal 300 over the communication network NW (step S201). More specifically, the data transmission unit 204 reads time-series data for the heart rate from the data storage unit 203 and transmits it to the relay terminal 300 over the communication network NW.

After receiving the time-series data for the biological information of the user 500 from the sensor terminal 200, the relay terminal 300 calculates an average as a representative value of the time-series data for the biological information (step S202). Next, the summarization unit 17 included in the relay terminal 300 calculates summary values which statistically summarize biological information over a certain period based on the average of the time-series data for the biological information calculated at step S202 (step S203).

Next, the measurement anomaly detection unit 305 detects as an anomaly that the averages of biological information that were used in the calculation of the summary values by the summarization unit 17 at step S203 are statistically insufficient for calculation of summary values (step S204). More specifically, the measurement anomaly detection unit 305 detects as an anomaly that the size of statistical samples of time-series data for biological information does not satisfy a sample size that can ensure statistically sufficient accuracy.

Then, the relay terminal 300 transmits the averages of the time-series data for the biological information, the summary values, and information indicating the anomaly to the external terminal 400 over the communication network NW (step S205). Then, the external terminal 400 receives the averages of the time-series data for the biological information, the summary values, and information indicating the anomaly. The external terminal 400 performs presentation processing based on the received averages, the summary values, and information indicating the anomaly (step S205), and causes the summary values and information indicating the anomaly to be displayed on the display device 109. The external terminal 400 may also generate and output assistance information for the user 500 based on the received averages, the summary values, and information indicating the anomaly.

As described above, with the biological information analysis apparatus 1A according to the second embodiment, the measurement anomaly detection unit 12 detects as an anomaly that averages of biological information or the occurrence ratio of biological state information values are statistically insufficient for calculation of summary values when the summarization unit 17 is to determine summary values. Accordingly, the user and the like can be informed that a statistically sufficient sample size has not been obtained for the calculated representative values for biological information and prompted to recognize it. Also, if the detected anomaly was due to an inadequate handling of the sensor 105, the user can be prompted to remedy the inadequate handling of the sensor 105 via presentation of information indicating the anomaly.

Third Embodiment

Next, a third embodiment of the present invention is described. In the following descriptions, the same components as those in the first and second embodiments are denoted with the same reference numerals and description thereof is omitted.

The first embodiment showed a case where the measurement anomaly detection unit 12 detects an anomaly contained in measured biological information based on time-series data with the representative values for biological information calculated by the data analysis unit 11. By contrast, in the third embodiment, the measurement anomaly detection unit 12 detects an anomaly based on the length of the period of time-series data with the representative values calculated by the data analysis unit 11. Also, a biological information analysis apparatus 1B according to the third embodiment further includes an outlier determination unit 18 that determines whether there are outliers or not in the biological information acquired by the sensor data acquisition unit 10.

Figure 10:
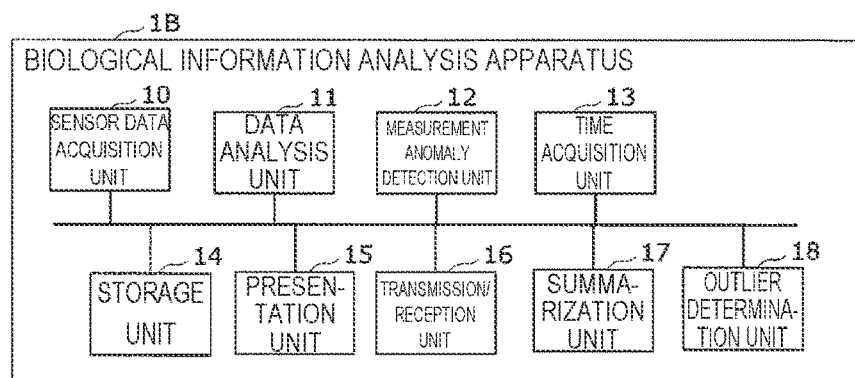
FIG. 10 is a block diagram showing a functional configuration of a biological information analysis apparatus according to a third embodiment.

As shown in FIG. 10, the outlier determination unit 18 determines whether time-series data for biological information contains outliers or not based on a preset criterion. The result of determination by the outlier determination unit 18 is input to the data analysis unit 11. More particularly, based on an upper threshold and a lower threshold predefined for the value of biological information, the outlier determination unit 18 invalidates a measured value of biological information exceeding the upper threshold and a measured value of biological information below the lower threshold. Biological information values from which outliers have been removed by the outlier determination unit 18 are input to the data analysis unit 11.

When it is determined that the time-series data for biological information contains outliers by the outlier determination unit 18, the data analysis unit 11 calculates an average of multiple pieces of biological information that were acquired at mutually corresponding times of measurement in the respective ones of multiple time intervals excluding that outlier as a representative value.

Regarding an output period during which time-series data with the representative values is output, the measurement anomaly detection unit 12 detects as an anomaly that the output period of the time-series data with the representative value that was actually output by the data analysis unit 11 is short relative to a predefined output period.

Operational Sequence of Biological Information Analysis System

Figure 11:
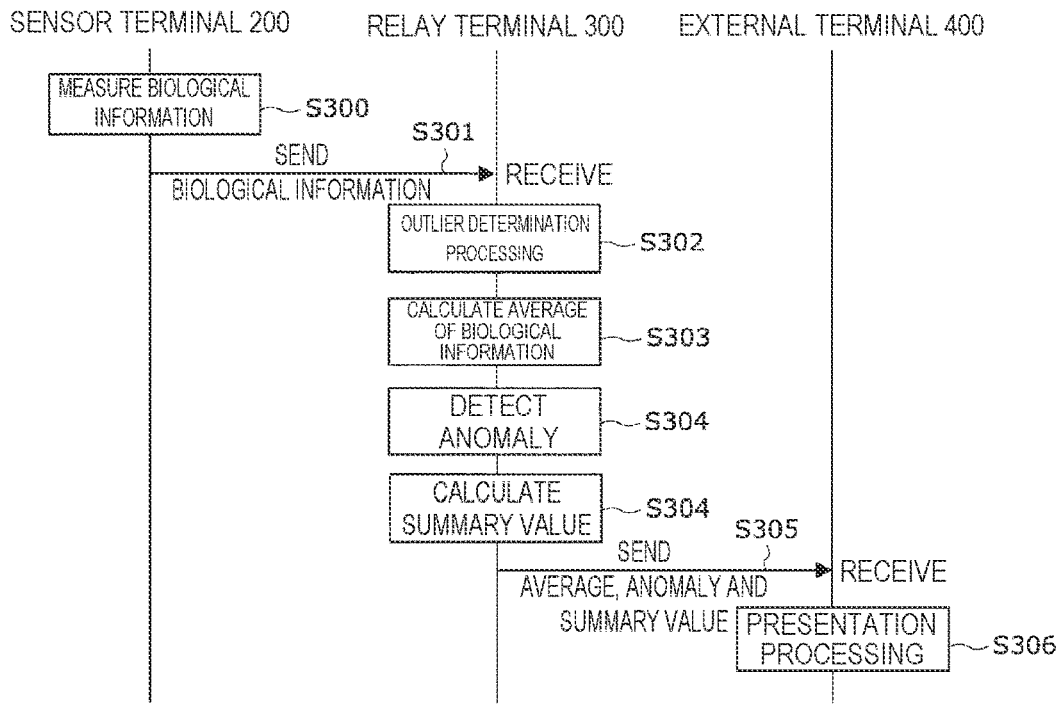
FIG. 11 is a sequence diagram illustrating operations of the biological information analysis system according to the third embodiment.

Next, operations in a case where the functions of the biological information analysis apparatus 1B according to this embodiment are implemented by a biological information analysis system including the sensor terminal 200, the relay terminal 300 and the external terminal 400 described in FIG. 5 are described with reference to the sequence diagram shown in FIG. 11. The respective functional blocks of the sensor terminal 200, the relay terminal 300, and the external terminal 400 are similar to the configurations described in FIG. 5. It is assumed that the relay terminal 300 includes the data analysis unit 11, the measurement anomaly detection unit 12, the summarization unit 17 and the outlier determination unit 18, and the external terminal 400 includes the presentation unit 15.

Initially, the sensor terminal 200 is attached to the user 500 and measures biological information of the user 500 for multiple time intervals (step S300). More specifically, the sensor terminal 200 measures the cardiac potentials of the user 500 with a heart rate meter (the sensor 201), for example. The sensor data acquisition unit 202 acquires the cardiac potentials from the sensor 201 and calculates a heart rate from electrocardiographic waveforms which are based on the cardiac potentials. The acquired cardiac potentials and the heart rate are stored in the data storage unit 203.

Next, the sensor terminal 200 transmits the measured biological information to the relay terminal 300 over the communication network NW (step S301). More specifically, the data transmission unit 204 reads time-series data for the heart rate from the data storage unit 203 and transmits it to the relay terminal 300 over the communication network NW.

After receiving the time-series data for the biological information of the user 500 from the sensor terminal 200, the outlier determination unit 18 of the relay terminal 300 determines whether the received time-series data for biological information contains outliers or not (step S302).

More specifically, the outlier determination unit 18 reads the upper threshold (e.g., 190 bpm) and the lower threshold (e.g., 40 bpm) of the heart rate stored in the data storage unit 302. The outlier determination unit 18 invalidates values exceeding the upper threshold and values below the lower threshold in the received biological information of the user 500.

For example, as shown in FIG. 12(a), a heart rate h1 of the user 500 in the first interval is below the lower threshold of 40 bpm in the time slot from 12 to 24 o'clock. A heart rate h2 of the user in the second interval is likewise below the lower threshold of 40 bpm in the time slots from 6 to 12 o'clock and from 18 to 24 o'clock. Therefore, the outlier determination unit 18 inputs heart rate values with the heart rate values below the lower threshold invalidated to the data analysis unit 11.

Next, based on the result of determination by the outlier determination unit 18, the data analysis unit 11 calculates an average of multiple pieces of biological information that were acquired at mutually corresponding times of measurement in the respective ones of multiple time intervals for the biological information of the user 500 (step S303). More particularly, the data analysis unit 11 uses the Formula (1) discussed above to calculate an average h3 of heart rates in the same time slots of the first and second intervals excluding those values that have been determined to be outliers, as shown in FIG. 12(*b*).

Figure 12:
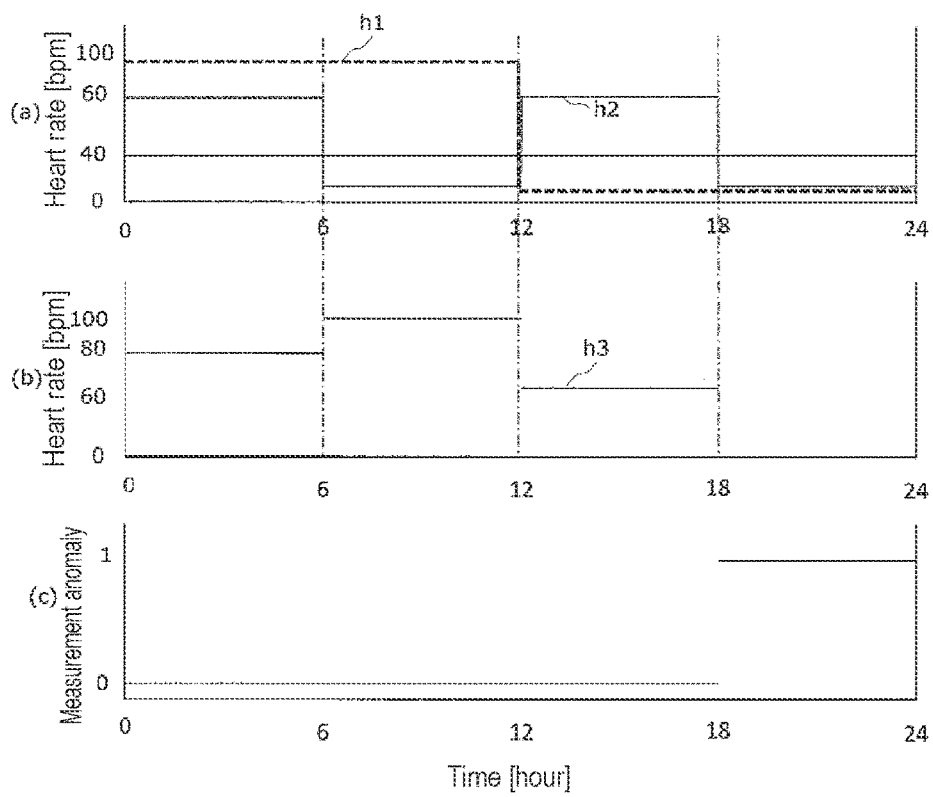
FIG. 12 is a diagram for describing detection of an anomaly according to the third embodiment.

As shown in FIG. 12(*b*), the average of heart rates from 0 to 6 o'clock in each interval is calculated to be 80 bpm, and the average of heart rates from 6 to 12 o'clock is calculated to be 100 bpm because outliers were invalidated. Similarly, the average of heart rates from 12 to 18 o'clock is calculated to be 60 bpm, and the average of heart rates from 18 to 24 o'clock is not calculated because both the heart rates in the first and second intervals are below the lower threshold. That is, in the time slots from 6 to 12 o'clock and from 12 to 18 o'clock, the number of data contained in the average At of heart rates is N=1 in Formula (1), and At is calculated as $A_t=(60)/1=60$ bpm, for example. For the time slot from 18 to 24 o'clock, a result of average calculation need not be returned as there is no data on the heart rate (empty).

By thus identifying outliers contained in biological information and removing the outliers from calculation in the averaging processing, the effect of outliers on the result of analysis on biological information can be reduced. Thus, measurements of biological information in concert with the biological behavior of the user 500 as a subject can be obtained regardless of measurement conditions of the sensor 201.

Referring back to FIG. 11, the measurement anomaly detection unit 305 detects as an anomaly that the actual output period of time-series data with the averages calculated based on biological information from which outliers have been removed is short relative to a predefined output period, regarding the output period during which the time-series data with the average is output (step S304). For example, as shown in FIG. 12(*b*), in the multiple heart rate averages calculated by the data analysis unit 304, the output period from 18 to 24 o'clock is empty of an output value of a heart rate average. In such a case, the actual output period of time-series data for averaged heart rates is 18 hours. While the output period predefined as the period of calculating an average heart rate is 24 hours, the actual output period of time-series data with the heart rate average is shorter than 24 hours by about 6 hours.

When time-series data with the averages of biological information having relatively many empty periods is output, the measurement anomaly detection unit 305 detects as an anomaly that sufficient confidence has not been obtained for an average value. The measurement anomaly detection unit 305 may, for example, determine the difference between 24 hours, namely the output period of time-series data predetermined as the period of calculating representative values, and the actual output period, and if the difference exceeds 2 hours, it may detect it as an anomaly. As shown in FIG. 12(*c*), no anomaly is detected in the time slot from 0 to 18 o'clock, while "1", or the value indicating an anomaly, is set in the time slot from 18 to 24 o'clock.

Referring back to FIG. 11, the summarization unit 17 included in the relay terminal 300 calculates statistical summary values based on the averages of biological information calculated at step S303 (step S304). Next, the relay terminal 300 transmits the calculated averages of multiple pieces of biological information, information indicating the anomaly, and the summary values to the external terminal 400 over the communication network NW (step S305).

Then, the external terminal 400 receives the averages of multiple pieces of biological information, information indicating the anomaly, and the summary values. The external terminal 400 performs presentation processing based on the received information (step S306), and displays the averages of biological information, information indicating the anomaly and the summary values on the display device. The external terminal 400 may further generate and output other assistance information for the user 500 based on the averages of biological information, information indicating the anomaly and the summary values.

Figure 13:
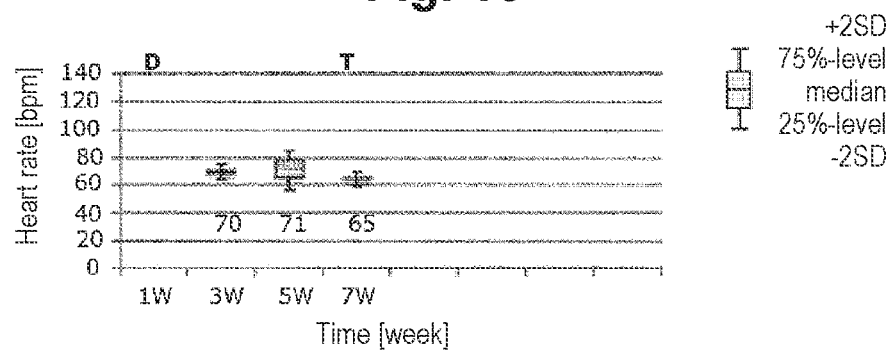
FIG. 13 is a diagram for describing an exemplary presentation of summary values according to the third embodiment.
Figure 14:
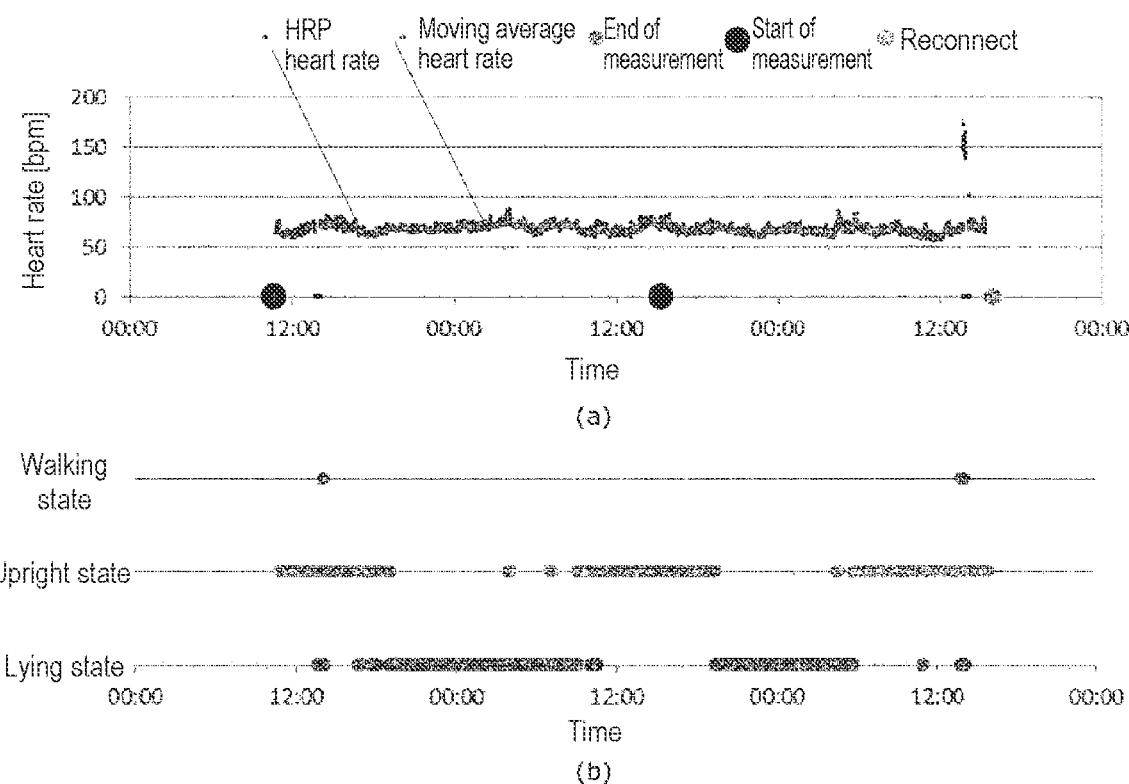
FIG. 14 is a diagram for describing detection of an anomaly according to a fourth embodiment.

For example, the presentation unit 404 may generate a graph as shown in FIG. 12(*c*) and cause it to be displayed on the display device 109 as information indicating the anomaly. Alternatively, the presentation unit 404 may cause box plots of the heart rate from the first through seventh weeks of the measurement period to be displayed on the display device 109 as the summary values of biological information such as shown in FIG. 13, for example. In FIG. 13, the 75%-level, average, and 25%-level of the heart rate are shown by boxes and a range of twice the positive and negative standard deviation (±2SD) is shown by whiskers. For example, as shown in FIG. 13, a label "T" may be displayed with the corresponding summary values as information indicating an anomaly when the difference between the predefined output period for time-series data with the averaged heart rate and the actual output period of average time-series data exceeds 2 hours.

Although the description above uses a quantitative variable such as heart rate as biological information, anomalies can be detected in a similar manner for a qualitative variable indicating the user's posture and the like instead of a quantitative variable. For example, assume a case where within a certain continuous period of 24 hours, biological state information acquired from the sensor 105 shows a lying state (40%), an upright state (60%), and a walking state (0%). In such a case, that no walking was observed for 24 hours at all could imply the presence of some circumstance such as a failure of the sensor 105 or the user being a wheelchair user.

For example, the measurement anomaly detection unit 305 may detect it as an anomaly when the proportion of a particular state (the walking state in the above example) is below 5%. Also, the presentation unit 404 may present a label "W", for example, as information indicating the anomaly with the summary values for which the anomaly has been detected. Taking such particular circumstances into account improves the usability of the biological information analysis apparatus 1B.

As has been described above, in the third embodiment, the measurement anomaly detection unit 12 detects as an anomaly that the output period of the time-series data with the representative values that was actually output by the data analysis unit 11 is short relative to a predefined output period, regarding the output period during which time-series data with the representative values is output. Also, the presentation unit 15 presents information indicating a detected anomaly. This can prompt the user and the like to recognize the occurrence of the anomaly and also to remedy the inadequacy that caused the anomaly, such as remedying an inadequate handling of the sensor 105 in preparation for subsequent measurement of biological information.

Fourth Embodiment

A fourth embodiment of the present invention is now described. In the following descriptions, the same components as those in the first to third embodiments are denoted with the same reference numerals and description thereof is omitted.

In the fourth embodiment, the measurement anomaly detection unit 12 detects as an anomaly that behavior of time-series data with the representative values calculated by the data analysis unit 11 fits in a predefined reference range. The configuration of the biological information analysis apparatus 1A according to the fourth embodiment is similar to that of the second embodiment (FIG. 7).

Heart rate as an example of biological information naturally varies in accordance with the user's life on one day, but some users have remarkably low variation. For example, when the user is taking a hypotensive drug for lowering the blood pressure, increase in the heart rate during activities is suppressed as a side effect. In such a case, normal heart rate variations cannot be obtained due to the medication of the user. It is thus desirable to pay specific attention in the calculation of summary values for measured heart rates.

FIG. 14(a) shows heart rate data for about 48 hours, and FIG. 14(b) shows the user's state at the corresponding times. Shown as the user's state are a walking state, an upright state, and a lying state in this order from the top. FIG. 14(b) shows the user's states that are calculated by the summarization unit 17 based on the time-series data for the user's heart rate (FIG. 14(a)).

As can be seen from FIG. 14(a), the user's heart rate remains almost flat over 48 hours. Also, as can be seen from FIG. 14(b), there is no noticeable difference arising in the heart rate value between the state of the user lying and the state of being upright.

Figure 15:
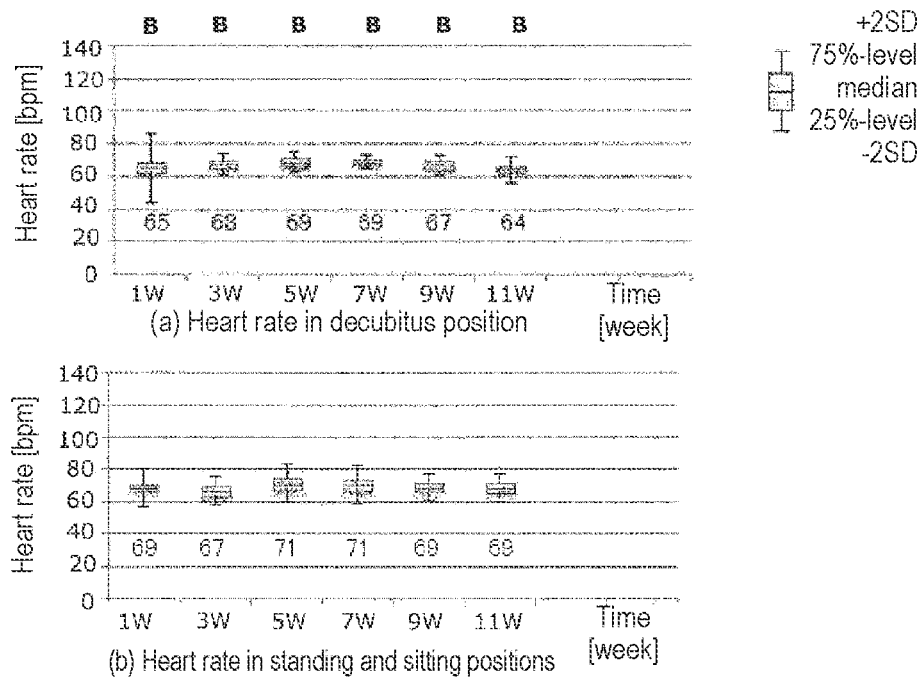
FIG. 15 is a diagram for describing an exemplary presentation of summary values according to the fourth embodiment.
Figure 16:
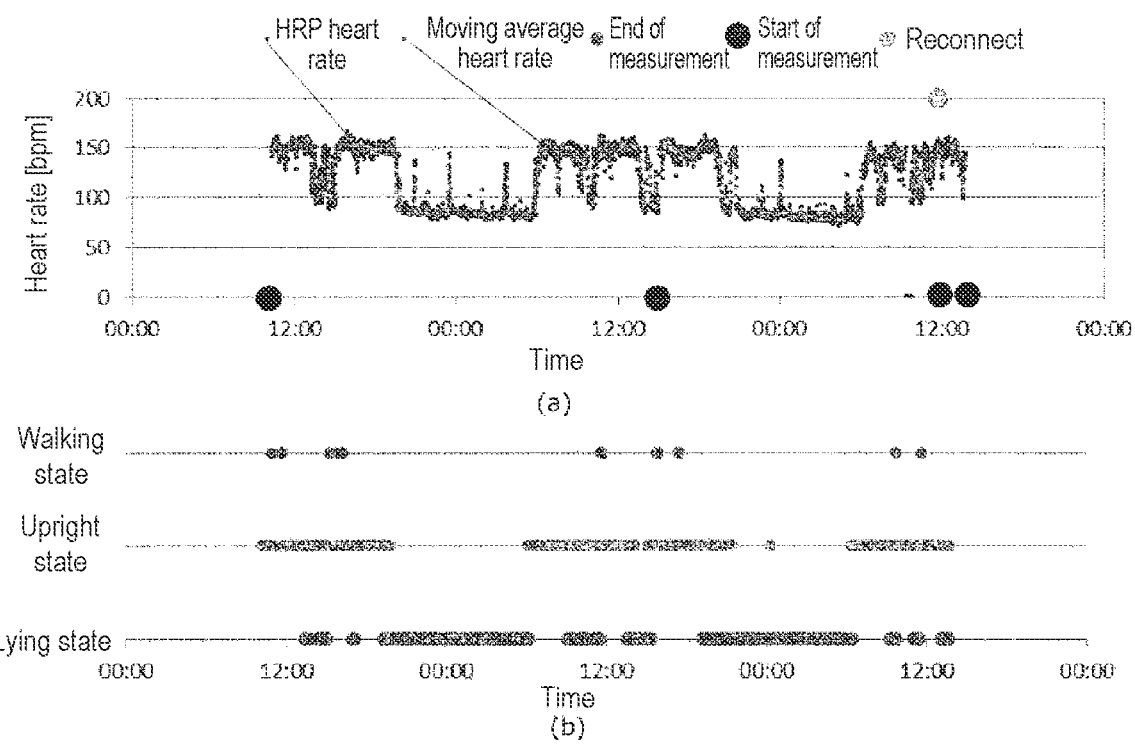
FIG. 16 is a diagram for describing detection of an anomaly according to a fifth embodiment.

FIG. 15 shows summary values generated by statistically summarizing of the user's states by the summarization unit 17 based on the occurrence ratio of the values indicating the user's states at mutually corresponding times of measurement in the respective ones of multiple time intervals. FIG. 15(a) shows box plots of heart rate averages when the user was in the lying state (in a decubitus position) as calculated summary values. FIG. 15(b) shows box plots of heart rate averages when the user was in an upright state (in standing and sitting positions) as calculated summary values.

The measurement anomaly detection unit 12 detects it as an anomaly when the heart rate averages in the standing position and the sitting position show behavior within the reference range not exceeding ±5 of the average of the heart rate in the decubitus position in the summary values shown in FIG. 15, for example. The measurement anomaly detection unit 12 may also set a reference range for an amount of change in the time-series data with the averages of biological information, such as heart rate, calculated by the data analysis unit 11, and may detect it as an anomaly when the behavior of the average time-series data fits in the set reference range.

The presentation unit 15 causes a label "B", for example, to be displayed on the display device 109 with the corresponding summary values as information indicating the anomaly detected by the measurement anomaly detection unit 12.

As has been described above, in the fourth embodiment, the measurement anomaly detection unit 12 detects as an anomaly that the behavior of time-series data for biological information calculated by the data analysis unit 11 is in a predefined reference range. Also, the presentation unit 15 outputs information indicating the detected anomaly. This can prompt the recognition of the fact that the state of the user's circulatory organ or the state of medication is in a special situation.

Fifth Embodiment

A fifth embodiment of the present invention is now described. In the following descriptions, the same components as those in the first to fourth embodiments are denoted with the same reference numerals and description thereof is omitted.

The fourth embodiment showed a case where the measurement anomaly detection unit 12 detects as an anomaly that the behavior of time-series data with the representative values calculated by the data analysis unit 11 fits in a predefined reference range. By contrast, in the fifth embodiment, the measurement anomaly detection unit 12 detects as an anomaly that the behavior of time-series data with representative values calculated by the data analysis unit 11 falls outside a predefined reference range. The configuration of the biological information analysis apparatus 1A according to the fifth embodiment is similar to that of the second embodiment (FIG. 7).

Heart rate as an example of biological information naturally varies in accordance with the user's life on one day, but some users have remarkably large variation. For example, it is known that a user with atrial fibrillation tachycardia shows an extremely large difference in the heart rate when the user is lying and when the user is upright. In such a case, normal heart rate variations cannot be obtained due to the disease of the user, so it is desirable to pay specific attention in calculating the summary values of the measured heart rate.

FIG. 16(a) shows heart rate data for about 48 hours and FIG. 16(b) shows the user's state at the corresponding times. Shown as the user's state are a walking state, an upright state, and a lying state in this order from the top. FIG. 16(b) shows the user's states that are calculated by the summarization unit 17 based on the time-series data for the user's heart rate (FIG. 16(a)).

As can be seen from FIG. 16(a), the change in the user's heart rate is extremely large over 48 hours. Also, as can be seen from FIG. 16(b), there is an extremely large difference in the value of the heart rate between the state of the user lying and the state of being upright.

Figure 17:
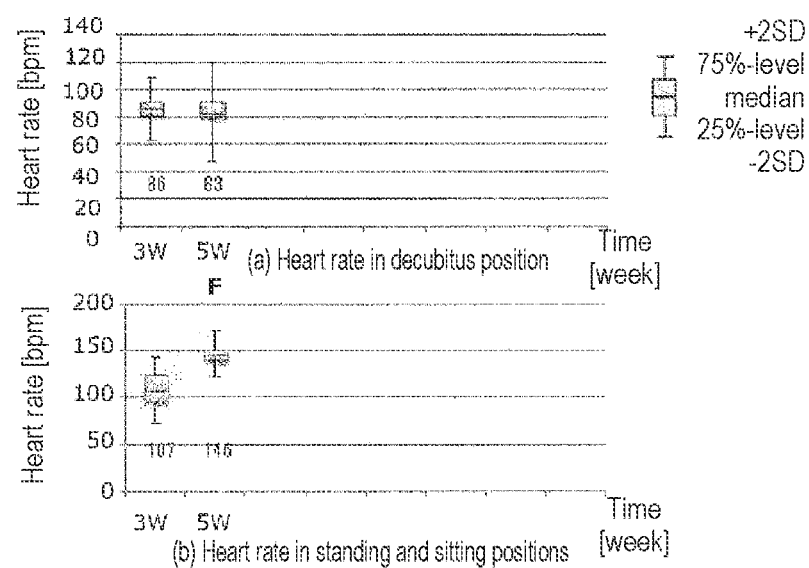
FIG. 17 is a diagram for describing an exemplary presentation of summary values according to the fifth embodiment.

FIG. 17 shows summary values generated by statistically summarizing of the user's states by the summarization unit 17 based on the occurrence ratio of the values indicating the user's states at mutually corresponding times of measurement in the respective ones of multiple time intervals. FIG. 17(a) shows box plots of heart rate averages when the user was in the lying state (in a decubitus position) as calculated summary values. FIG. 17(b) shows box plots of heart rate averages when the user was in an upright state (in standing and sitting positions) as calculated summary values.

The measurement anomaly detection unit 12 detects an anomaly of lying outside the predefined reference range when the average of heart rates during a standing position and a sitting position is greater than the average of heart rates during a decubitus position by 40 or more in the summary values shown in FIG. 17, for example. The measurement anomaly detection unit 12 may also set a reference range for an amount of change in the time-series data with the averages of the heart rate and the like calculated by the data analysis unit 11, and may detect as an anomaly that the behavior of the average time-series data falls outside the set reference range.

The presentation unit 15 causes a label "F", for example, to be displayed on the display device 109 with the corresponding summary values as information indicating the anomaly detected by the measurement anomaly detection unit 12.

As has been described above, in the fifth embodiment, the measurement anomaly detection unit 12 detects as an anomaly that the behavior of time-series data for biological information calculated by the data analysis unit 11 falls outside a predefined reference range. Also, the presentation unit 15 outputs information indicating the detected anomaly. This can prompt the recognition of the fact that the state of the user's circulatory organ or the state of medication is in a special situation.

Sixth Embodiment

A sixth embodiment of the present invention is now described. In the following descriptions, the same components as those in the first to fifth embodiments are denoted with the same reference numerals and description thereof is omitted.

The third embodiment showed a case where the outlier determination unit 18 determines whether multiple pieces of biological information acquired by the sensor data acquisition unit 10 contain outliers or not based on a preset criterion. By contrast, in the sixth embodiment, when the outlier determination unit 18 determines that outliers are contained, the measurement anomaly detection unit 12 detects as an anomaly that the proportion of outliers contained in time-series data for multiple pieces of biological information exceeds a predetermined value.

The biological information analysis apparatus 1B according to the sixth embodiment has a similar configuration to that of the biological information analysis apparatus 1B described in the third embodiment. The biological information analysis apparatus 1B includes the sensor data acquisition unit 10, the data analysis unit 11, the time acquisition unit 13, the storage unit 14, the presentation unit 15, the transmission/reception unit 16, the summarization unit 17, and the outlier determination unit 18 as shown in FIG. 10.

The outlier determination unit 18 invalidates a measured value of biological information exceeding an upper threshold and a measured value of biological information below a lower threshold based on an upper threshold and a lower threshold preset for the value of biological information acquired by the sensor data acquisition unit 10.

The measurement anomaly detection unit 12 detects as an anomaly that the proportion of outliers contained in time-series data for multiple pieces of biological information exceeds a predetermined value. More particularly, when the outlier determination unit 18 determines that there are biological information values exceeding the upper threshold or values below the lower threshold, the measurement anomaly detection unit 12 detects as an anomaly that the number of values exceeding the upper threshold or values below the lower threshold is greater than a certain number in the time-series data for the multiple pieces of biological information acquired by the sensor data acquisition unit 10.

The presentation unit 15 causes information indicating the anomaly detected by the measurement anomaly detection unit 12 to be displayed on the display device 109. The presentation unit 15 may also cause information indicating the anomaly to be displayed on the display device 109 with the representative values calculated by the data analysis unit 11 and/or the summary values calculated by the summarization unit 17.

Figure 18:
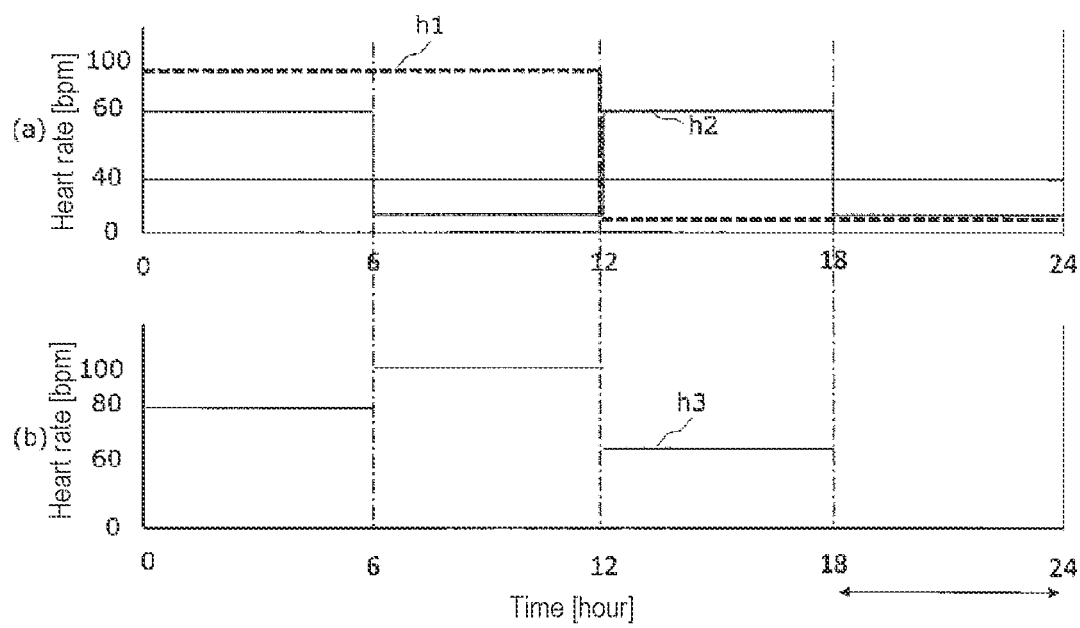
FIG. 18 is a diagram for describing outlier determination according to a sixth embodiment.

As shown in FIG. 18(*a*), a heart rate h1 of the user in the first interval acquired by the sensor data acquisition unit 10 is below a lower threshold of 40 bpm in the time slot from 12 to 24 o'clock. Also, a heart rate h2 of the user in the second interval is similarly below the lower threshold of 40 bpm in the time slots from 6 to 12 o'clock and from 18 to 24 o'clock. The outlier determination unit 18 inputs heart rate values with the heart rate values below the lower threshold invalidated to the data analysis unit 11.

Here, the data analysis unit 11 is described for a case where it calculates a representative value for biological information in each 6-hour output period in time-series data for biological information as shown in FIG. 18(*b*), for example.

As shown in FIG. 18(*a*), the measurement anomaly detection unit 12 detects it as an anomaly when the proportion of outliers contained in the time-series data exceeds a predetermined value, e.g., when the period during which the value of biological information acquired by the sensor data acquisition unit 10 was below the lower threshold is 2 hours, for example. The presentation unit 15 may also cause information indicating the period during which the duration of the biological information value being below the lower threshold is 2 hours or more (from 18 to 24 o'clock) to be displayed on the display device 109 as information indicating an anomaly.

The data analysis unit 11 calculates an average of multiple pieces of biological information that were acquired at mutually corresponding times of measurement in the respective ones of multiple time intervals for the user's biological information based on the result of determination by the outlier determination unit 18. More particularly, the data analysis unit 11 calculates an average h3 of heart rates in the same time slots of the first and the second intervals excluding the values determined to be outliers in each reference period, as shown in FIG. 18(*b*).

As shown in FIG. 18(*b*), the average of the heart rates from 0 to 6 o'clock in each interval (the first day and the second day) is calculated to be 80 bpm, and the average of the heart rates from 6 to 12 o'clock is calculated to be 100 bpm because outliers have been invalidated. Similarly, the average of the heart rates from 12 to 18 o'clock is calculated to be 60 bpm, while the average of the heart rates from 18 to 24 o'clock is not calculated because both the heart rates in the first and second intervals are below the lower threshold.

The summarization unit 17 calculates summary values which statistically summarize multiple pieces of biological information for each given period included in multiple time intervals (e.g., the first day and the second day), based on the time-series data with representative values for multiple pieces of biological information calculated by the data analysis unit 11. For example, the summarization unit 17 calculates summary values, such as standard deviation, of biological information for each given period such as one hour, one day, one week, one month, and one year. The calculated summary values of biological information are displayed on the display device 109 and the like via the presentation unit 15.

Figure 19:
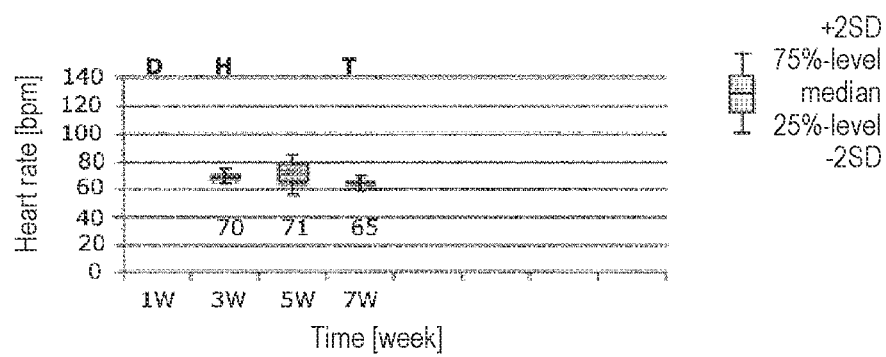
FIG. 19 is a diagram for describing an exemplary presentation of summary values according to the sixth embodiment.

The presentation unit 15 may also cause box plots of the heart rate from the first through seventh weeks of the measurement period, for example, to be displayed on the display device 109 as the summary values of biological information as shown in FIG. 19. In FIG. 19, the 75%-level, average, and 25%-level of the heart rate are shown by boxes and a range of twice the positive and negative standard deviation (±2SD) is shown by whiskers.

As shown in FIG. 19, the presentation unit 15 may also cause a label "H", for example, to be displayed on the display device 109 with the corresponding summary values as information indicating the anomaly detected by the measurement anomaly detection unit 12.

As described above, in the biological information analysis apparatus 1B according to the sixth embodiment, when the outlier determination unit 18 determines that an outlier is contained in the values of biological information acquired by the sensor data acquisition unit 10, the data analysis unit 11 calculates a representative value for biological information excluding the outlier. This can reduce the effect of outliers on calculated representative values. Furthermore, the measurement anomaly detection unit 12 detects as an anomaly that the proportion of outliers contained in time-series data for biological information as determined by the outlier determination unit 18 exceeds a predetermined value.

When outliers are contained in measured biological information, there might have been some trouble in the measurement condition of biological information, such as the state of attachment of the sensor 105. Accordingly, in addition to removing outliers when a representative value is calculated by the outlier determination unit 18, the user can be informed of the trouble in measurement information for biological information as well. Thus, the user can be prompted to recognize possible trouble in the measurement condition of biological information.

While embodiments of the biological information analysis apparatus, the biological information analysis method, and the biological information analysis system according to embodiments of the present invention have been described, the present invention is not limited to the described embodiments and various modifications conceivable by those skilled in the art may be made within the scope of the invention as set forth in the claims.

Although the embodiments were described for the case of cardiac potential or acceleration as examples of biological information that is measured and calculated by the sensor 105, 201, biological information is not limited to them and may also be myogenic potential, heartbeat, pulse, blood pressure, respiration, posture, walking, speed of travel, location, action, exercise intensity, body motion, active mass etc., for example.

Also, the described embodiments showed a case where the relay terminal 300 includes the data analysis unit 11 as a specific example. However, the functions provided in the data analysis unit 11 may be distributed among the sensor terminal 200, the relay terminal 300, and the external terminal 400.

For example, the sensor terminal 200 having a first data analysis unit, the relay terminal 300 having a second data analysis unit, and the external terminal 400 having a third data analysis unit may cooperatively analyze time-series data for biological information over multiple time intervals, and from multiple pieces of biological information that were acquired at mutually corresponding times of measurement in respective ones of multiple time intervals, calculate representative values for these multiple pieces of biological information.

In addition, the described embodiments may be combined with each other, and the biological information analysis apparatus 1, 1A, 1B is each able to analyze biological information that is classified as a quantitative variable such as heart rate and biological information (biological state information) that is classified as a qualitative variable such as the user's state.

REFERENCE SIGNS LIST 1 biological information analysis apparatus
10, 202 sensor data acquisition unit
11, 304 data analysis unit
12, 305 measurement anomaly detection unit
13, 303 time acquisition unit
14 storage unit
15, 404 presentation unit
16 transmission/reception unit
101 bus
102 CPU
103 main storage
104 communication interface
105, 201 sensor
106 auxiliary storage
107 clock
108 input/output device
109 display device
200 sensor terminal
300 relay terminal
400 external terminal
203, 302, 402 data storage unit
204, 306 data transmission unit
301, 401 data reception unit
403 presentation processing unit

The invention claimed is:

1. A biological information analysis apparatus comprising:
   one or more processors; and
   a storage device storing a program to be executed by the one or more processors, the program including instructions for:
   acquiring biological information measured by a sensor;
   analyzing time-series data for the biological information over a plurality of time intervals and, from multiple pieces of biological information that were acquired at mutually corresponding times of measurement in respective ones of the plurality of time intervals, calculating representative values for the multiple pieces of biological information;
   determining whether an anomaly is contained in the measured biological information based on time-series data of the representative values calculated by the data analyzer or based on the time-series data for the multiple pieces of biological information;
   outputting the representative values for the multiple pieces of biological information and, in response to a determination that the anomaly is contained in the measured biological information, information indicating the anomaly;
   determining whether the multiple pieces of biological information contain outliers or not based on a preset criterion;
   in response to a determination that the multiple pieces of biological information contain the outliers, calculating representative values for multiple pieces of biological information that were acquired at mutually corresponding times of measurement in respective ones of the plurality of time intervals, from the multiple pieces of biological information excluding the outliers; and
   determining as the anomaly that an output period during which time-series data with the representative values was output is short relative to a predefined output period, regarding the output period during which the time-series data with the representative values is output.

2. The apparatus according to claim 1, wherein the program further includes instructions for:
   determining whether the multiple pieces of biological information contain outliers or not based on a preset criterion; and determining whether a proportion of the outliers contained in the time-series data for the multiple pieces of biological information exceeds a predetermined value; and in response to a determination that the proportion of the outliers exceeds the predetermined value, determining that the proportion of the outliers exceeding the predetermined value is the anomaly.

3. The apparatus according to claim 1, wherein the program further includes instructions for:

calculating averages of the multiple pieces of biological information as the representative values;

in response to the averages being statistically sufficient, calculating summary values which statistically summarize the multiple pieces of biological information for each given period included in the plurality of time intervals based on time-series data with the averages of the multiple pieces of biological information; and detecting as the anomaly that the averages are statistically insufficient for calculation of the summary values at a time in which the summary values are to be calculated.

4. The apparatus according to claim 3, wherein the program further includes instructions for:

calculating biological state information being a qualitative variable based on the time-series data for the biological information over the plurality of time intervals, and calculating summary values which statistically summarize the biological state information based on an occurrence ratio of values of the biological state information at mutually corresponding times of measurement in the respective ones of the plurality of time intervals; and detecting as the anomaly that the occurrence ratio of values of biological state information is statistically insufficient for calculation of the summary values at a time in which the summary values are to be calculated.

5. The apparatus according to claim 1, wherein the program further includes instructions for detecting as the anomaly that behavior of the time-series data with the representative values falls outside a predefined reference range.

6. A biological information analysis method comprising:

a sensor data acquisition step of acquiring biological information measured by a sensor;

a data analysis step of analyzing time-series data for the biological information over a plurality of time intervals and, from multiple pieces of biological information that were acquired at mutually corresponding times of measurement in respective ones of the plurality of time intervals, calculating representative values for the multiple pieces of biological information;

a measurement anomaly detection step of detecting whether an anomaly is contained in the measured biological information based on time-series data of the representative values calculated at the data analysis step or based on the time-series data for the multiple pieces of biological information;

a presentation step of outputting the representative values for the multiple pieces of biological information and, in a case in which the anomaly is contained in the measured biological information, information indicating the anomaly;

an outlier determination step of determining whether the multiple pieces of biological information contain outliers or not based on a preset criterion;

in response to a determination that the outliers are contained, calculating representative values for multiple pieces of biological information that were acquired at mutually corresponding times of measurement in respective ones of the plurality of time intervals, from the multiple pieces of biological information excluding the outliers; and detecting as the anomaly that an output period during which time-series data with the representative values was output is short relative to a predefined output period, regarding the output period during which the time-series data with the representative values is output.

7. The method according to claim 6, further comprising an outlier determination step of determining whether the multiple pieces of biological information contain outliers or not based on a preset criterion, wherein the method further comprises detecting as the anomaly that a proportion of the outliers contained in the time-series data for the multiple pieces of biological information exceeds a predetermined value.

8. The method according to claim 6, further comprising:

calculating averages of the multiple pieces of biological information as the representative values;

in response to the averages being statistically sufficient, a first summarization step of calculating summary values which statistically summarize the multiple pieces of biological information for each given period included in the plurality of time intervals based on time-series data with the averages of the multiple pieces of biological information; and detecting as the anomaly that the averages are statistically insufficient for calculation of the summary values when the summary values are calculated in the first summarization step.

9. The method according to claim 8, further comprising:

a second summarization step of calculating biological state information being a qualitative variable based on the time-series data for the biological information over the plurality of time intervals, and calculating summary values which statistically summarize the biological state information based on an occurrence ratio of values of the biological state information at mutually corresponding times of measurement in the respective ones of the plurality of time intervals; and detecting as the anomaly that the occurrence ratio of values of biological state information is statistically insufficient for calculation of the summary values when the summary values are calculated in the second summarization step.

10. The method according to claim 6, further comprising detecting as the anomaly that behavior of the time-series data with the representative values calculated in the data analysis step falls outside a predefined reference range.

11. A biological information analysis system comprising:

a sensor terminal configured to output biological information measured by a sensor worn by a user to outside;

a relay terminal configured to receive the biological information output by the sensor terminal and output the received biological information to outside; and an external terminal configured to receive the biological information output by the sensor terminal or by the relay terminal and cause the received biological information to be displayed on a display device, wherein at least one of the sensor terminal, the relay terminal, and the external terminal comprises one or more processors and a storage device storing a program to be executed by the one or more processors, the program including instructions for:

acquiring the biological information;

analyzing time-series data for the biological information over a plurality of time intervals and, from multiple pieces of biological information that were acquired at mutually corresponding times of measurement in respective ones of the plurality of time intervals, calculating representative values for the multiple pieces of biological information;

determining whether an anomaly is contained in the measured biological information based on time-series data of the calculated representative values or based on the time-series data for the multiple pieces of biological information;

calculating averages of the multiple pieces of biological information as the representative values;

in response to the averages being statistically sufficient, calculating summary values which statistically summarize the multiple pieces of biological information for each given period included in the plurality of time intervals based on time-series data with the averages of the multiple pieces of biological information; and detecting as the anomaly that the averages are statistically insufficient for calculation of the summary values at a time in which the summary values are to be calculated; and outputting the representative values for the multiple pieces of biological information and, in a case in which it is determined the anomaly is contained in the measured biological information, information indicating the anomaly.

12. The biological information analysis system according to claim 11, wherein the program further includes instructions for:

calculating biological state information being a qualitative variable based on the time-series data for the biological information over the plurality of time intervals, and calculating summary values which statistically summarize the biological state information based on an occurrence ratio of values of the biological state information at mutually corresponding times of measurement in the respective ones of the plurality of time, intervals; and detecting as the anomaly that the occurrence ratio of values of biological state information is statistically insufficient for calculation of the summary values at a time in which the summary values are to be calculated.

13. The biological information analysis system according to claim 11, wherein the program further-includes instructions for:

determining whether the multiple pieces of biological information contain outliers or not based on a preset criterion;

in response to a determination that the multiple pieces of biological information contain the outliers, calculating representative values for multiple pieces of biological information that were acquired at mutually corresponding times of measurement in respective ones of the plurality of time intervals, from the multiple pieces of biological information excluding the outliers; and determining as the anomaly that an output period during which time-series data with the representative values was output is short relative to a predefined output period, regarding the output period during which the time-series data with the representative values is output.

* * * * *